US012636247B2

(12) United States Patent
Hata

(10) Patent No.: US 12,636,247 B2
(45) Date of Patent: May 26, 2026

(54) COSMETIC

(71) Applicant: SHIN-ETSU CHEMICAL CO., LTD., Tokyo (JP)

(72) Inventor: Ryunosuke Hata, Takasaki (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 813 days.

(21) Appl. No.: 17/922,414

(22) PCT Filed: Apr. 5, 2021

(86) PCT No.: PCT/JP2021/014447
§ 371 (c)(1),
(2) Date: Oct. 31, 2022

(87) PCT Pub. No.: WO2021/229953
PCT Pub. Date: Nov. 18, 2021

(65) Prior Publication Data

US 2023/0263720 A1 Aug. 24, 2023

(30) Foreign Application Priority Data

May 13, 2020 (JP) ................................ 2020-084771

(51) Int. Cl.
*A61K 8/891* (2006.01)

(52) U.S. Cl.
CPC .......... *A61K 8/891* (2013.01); *A61K 2800/10* (2013.01); *A61K 2800/594* (2013.01)

(58) Field of Classification Search
CPC ................ A61K 8/891; A61K 2800/10; A61K 2800/594
See application file for complete search history.

(56) References Cited

U.S. PATENT DOCUMENTS 5,476,912 A 12/1995 Hosoi et al.
2005/0281769 A1 12/2005 Toumi
(Continued)

FOREIGN PATENT DOCUMENTS

CN 101951882 A 1/2011
CN 103459446 A 12/2013
(Continued)

OTHER PUBLICATIONS

Fei, "Effect of Hard and Soft Monomers on Polysiloxane/Acrylate Composite Emulsion," China Adhesives, vol. 28, No. 1, pp. 1-7.
Tran et al., "Dynamics of Pseudomonas Aeruginosa Association with Anionic Hydrogel Surfaces in the Presence of Aqueous Divalent-Cation Salts," Journal of Colloid and Interface Science, 2011, vol. 362, pp. 58-66.
Nov. 5, 2023 Search Report issued in Chinese Patent Application No. 202180034164.4.
Jun. 6, 2021 Search Report issued in International Patent Application No. PCT/JP2021/014447.
(Continued)

*Primary Examiner* — Shane Fang
(74) *Attorney, Agent, or Firm* — OLIFF PLC.

(57) ABSTRACT

A cosmetic contains a high molecular weight polymer that is an addition polymerization product between: a polymer crosslinking agent of a (meth)acrylic-based graft silicone having a main chain with (meth)acrylic-based repeating units represented by the following formulae (I), (II), and (III), and side chains with unsaturated bonds and an organopolysiloxane structure; and an organohydrogen polysiloxane represented by the following general formula (4). A represents a group selected from an alkoxy group having 1 to 22 carbon atoms and an aryloxy group having 6 to 20 carbon atoms. B represents a group having an unsaturated bond represented by the following formula (1). C represents a group represented by the following formula (2), (3-1), or (3-2).

(I)

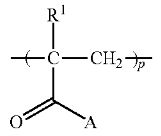

(II)

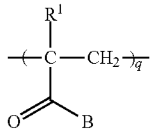

(III)

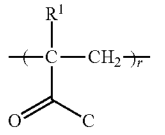

(1)

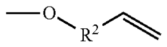

(2)

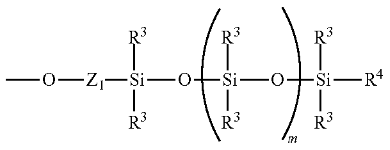

(3-1)

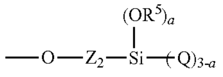

(3-2)

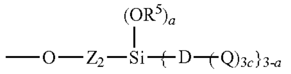

6 Claims, No Drawings

(56) References Cited

U.S. PATENT DOCUMENTS

| | | | | |
|---|---|---|---|---|
| 2007/0181553 | A1* | 8/2007 | Stanzel | B23K 9/124 219/137.71 |
| 2009/0151086 | A1* | 6/2009 | Brun | A61K 8/8152 8/405 |
| 2010/0221296 | A1 | 9/2010 | Moneuze et al. | |
| 2010/0284957 | A1 | 11/2010 | Yamada et al. | |
| 2014/0018508 | A1 | 1/2014 | Masubuchi et al. | |
| 2016/0262991 | A1 | 9/2016 | Akabane et al. | |
| 2017/0233514 | A1* | 8/2017 | Yamamoto | B32B 7/06 523/435 |
| 2019/0248945 | A1 | 8/2019 | Hata | |
| 2021/0017199 | A1 | 1/2021 | Hata | |

FOREIGN PATENT DOCUMENTS

| | | | |
|---|---|---|---|
| EP | 1084694 | A1 | 3/2001 |
| EP | 1 992 656 | A1 | 11/2008 |
| EP | 3 208 322 | A1 | 8/2017 |
| EP | 3 527 592 | A1 | 8/2019 |
| EP | 3 766 908 | A1 | 1/2021 |
| JP | 863-152308 | A | 6/1988 |
| JP | H01-207354 | A | 8/1989 |
| JP | H04-272932 | A | 9/1992 |
| JP | H07-70246 | A | 3/1995 |
| JP | 2016-169324 | A | 9/2016 |
| JP | 2019-137775 | A | 8/2019 |
| JP | 2021-014548 | A | 2/2021 |
| WO | 2004/024798 | A1 | 3/2004 |

OTHER PUBLICATIONS

Nov. 15, 2022 International Preliminary Report on Patentability issued in International Application No. PCT/JP2021/014447.

May 22, 2024 extended Search Report issued in European Patent Application No. 21804113.5.

* cited by examiner

COSMETIC

TECHNICAL FIELD

The present invention relates to a cosmetic.

BACKGROUND ART

Patent Document 1 discloses that a specific organopolysiloxane polymerized product obtained by subjecting an organohydrogen polysiloxane and an organopolysiloxane having at least two aliphatic unsaturated bonding groups to addition polymerization can be a cosmetic base material which is soft and excellent in stability. The organopolysiloxane polymerized product has been used in many cosmetics. Generally, this product is swollen with a liquid oil to prepare a paste-state composition, which is used to thicken a cosmetic and to stabilize an emulsified composition.

Meanwhile, liquid oils such as silicone oil, hydrocarbon oil, ester oil, natural animal or vegetable oil, and semi-synthetic oil are used in cosmetics. In particular, ester oil is frequently used in suncare products because of its high ability to dissolve ultraviolet absorbers. However, it is known that the organopolysiloxane polymerized product is hardly swollen with an oil agent having high polarity, such as ester oil.

To solve such a problem, Patent Documents 2 and 3 disclose that an organopolysiloxane polymerized product modified by a long-chain alkyl group, a polyether chain or a polyglycerin chain, and a paste-state silicone composition in which silicone oil is added to swell the polymerized product provide cosmetics excellent in storage stability. However, although the polymerized products disclosed in Patent Documents 2 and 3 can be swollen with ester oil, the affinity for ester oil is insufficient. Hence, there is room for improvement in storage stability and feeling on use of cosmetics containing these.

CITATION LIST

Patent Literature

Patent Document 1: JP H01-207354A
Patent Document 2: JP H04-272932A
Patent Document 3: WO 2004/024798A1

SUMMARY OF INVENTION

Technical Problem

The present invention has been made in view of the above-mentioned circumstance, and an object thereof is to provide a cosmetic excellent in storage stability and feeling on use by blending a high molecular weight polymer having high affinity for liquid oil agents.

Solution to Problem

To solve the problems, the present invention provides a cosmetic which comprises a high molecular weight polymer comprising an addition polymerization product of:

a polymer crosslinking agent comprising a (meth)acrylic-based graft silicone having a main chain with (meth) acrylic-based repeating units represented by the following formulae (I), (II), and (III), and side chains with unsaturated bonds and an organopolysiloxane structure; and an organohydrogen polysiloxane represented by the following general formula (4).

(I)

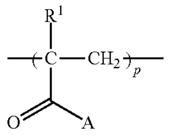

(II)

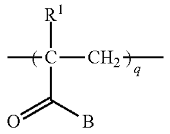

(III)

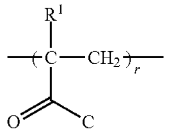

In the formulae, $R^1$'s each independently represent a hydrogen atom or a methyl group. A represents a group selected from an alkoxy group having 1 to 22 carbon atoms and an aryloxy group having 6 to 20 carbon atoms. B represents a group having an unsaturated bond represented by the following formula (1).

(1)

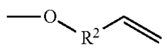

In the formula, $R^2$ represents a single bond, or a substituted or unsubstituted divalent hydrocarbon group having 1 to 20 carbon atoms and optionally containing an oxygen atom at a position not adjacent to any oxygen in the formula (1).

C represents a group having a linear organopolysiloxane structure represented by the following formula (2), or a group having a dendritic organopolysiloxane structure represented by the following (3-1) or (3-2).

(2)

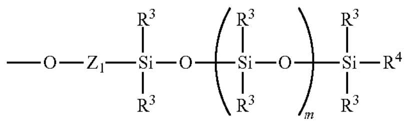

In the formula (2), $Z_1$ represents a divalent organic group, $R^3$'s each independently represent a saturated hydrocarbon group having 1 to 10 carbon atoms or a phenyl group, $R^4$ represents a saturated hydrocarbon group having 1 to 10 carbon atoms, and "m" represents an integer of 0 to 100.

(3-1)

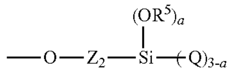

(3-2)

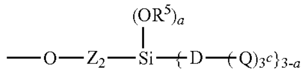

In the formulae (3-1) and (3-2), $Z_2$ represents a divalent organic group, "a" represents a number of 0 to 3, Q represents a group represented by the following formula (3), D represents an organopolysiloxanyl group having a dendritic structure with a hierarchical number of "c" and a valence of $3^c+1$, that is, "3 to the $c^{th}$ power"+1, and "c" represents an integer of 1 to 8.

(3)

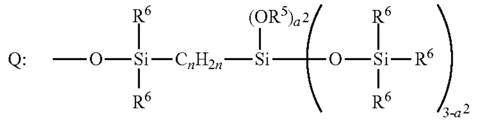

$R^5$ represents a saturated hydrocarbon group having 1 to 10 carbon atoms or a phenyl group, $R^6$ represents a saturated hydrocarbon group having 1 to 8 carbon atoms or a phenyl group, $R^7$ represents a hydrogen atom, a saturated hydrocarbon group having 1 to 10 carbon atoms, or a phenyl group, $a^2$ represents a real number of 0 to 2, and "n" represents an integer of 2 to 12.

An order of bonding of the repeating units represented by the formulae (I), (II), and (III) is not limited. "q" and "r" are not 0, and "p", "q" and "r" represent integers and are such numbers that the polymer crosslinking agent has a number-average molecular weight of 1,000 to 1,000,000 g/mol.

$$M_xD_yT_zQ_w \quad (4)$$

In the formula, M represents a siloxane unit of $R^8{}_3SiO_{1/2}$, D represents a siloxane unit of $R^8{}_2SiO_{2/2}$, T represents a siloxane unit of $R^8SiO_{3/2}$, and Q represents a siloxane unit of $SiO_{4/2}$; $R^8$'s each independently represent a hydrogen atom, a substituted or unsubstituted alkyl group having 1 to 10 carbon atoms, or a substituted or unsubstituted aryl group having 6 to 22 carbon atoms; at least two of the siloxane units contain hydrogen atoms; "x", "y", "z", and "w" each represent 0 or a positive number, provided that $y+z+w \geq 1$, and are such numbers that the organohydrogen polysiloxane represented by the general formula (4) has a number-average molecular weight of 500 to 900,000 g/mol; and an order of bonding of the siloxane units represented by M, D, T, and Q is not limited.

Such a cosmetic is excellent in storage stability and feeling on use.

Moreover, in the present invention, C in the repeating unit (III) can be a group having a linear organopolysiloxane structure represented by the formula (2).

Such a cosmetic can further enhance the effects of the present invention.

Further, in the present invention can comprise a composition comprising the high molecular weight polymer swollen with a liquid oil agent.

Such a cosmetic is more excellent in storage stability.

Further, in the present invention, the liquid oil agent can be an ester oil.

Such a cosmetic is more excellent in storage stability and feeling on use.

Furthermore, the present invention can further comprise water, wherein the cosmetic is in a form of emulsion.

Such a cosmetic is further excellent in feeling on use.

Advantageous Effects of Invention

As described above, the high molecular weight polymer that is an addition polymerization product between a (meth) acrylic-based graft silicone as a polymer crosslinking agent and an organohydrogen polysiloxane has many ester bonds. Thereby, the high molecular weight polymer has high affinity for an ester oil and a polar oil among liquid oil agents, and is capable of readily swelling therewith. Thus, when this high molecular weight polymer is blended in a cosmetic, the resulting composition also containing such a polar oil as an ester oil has high storage stability and excellent feeling on use in comparison with those with normal silicone polymers.

DESCRIPTION OF EMBODIMENTS

As noted above, there have been demands for the development of a cosmetic excellent in storage stability and feeling on use.

The present inventor has devoted ingenuity and consequently found that when a polymer crosslinking agent of a graft polymer having a (meth)acryl group-based main chain and side chains with unsaturated bonds and an organopolysiloxane structure is subjected to addition polymerization with an organohydrogen polysiloxane, a high molecular weight polymer obtained thereby has high affinity for such a polar oil as an ester oil among liquid oil agents. Particularly, the inventor has found that blending a cosmetic with a paste-like composition containing the high molecular weight polymer swollen with a liquid oil agent can improve the storage stability and feeling on use. These findings have led to the completion of the present invention.

Specifically, the present invention is a cosmetic which comprises a high molecular weight polymer comprising an addition polymerization product of:

a polymer crosslinking agent comprising a (meth)acrylic-based graft silicone having a main chain with (meth) acrylic-based repeating units represented by the following formulae (I), (II), and (III), and side chains with unsaturated bonds and an organopolysiloxane structure; and an organohydrogen polysiloxane represented by the following general formula (4).

(I)

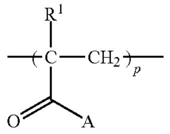

(II)

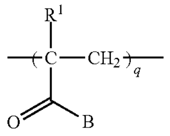

(III)

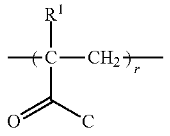

In the formulae, $R^1$'s each independently represent a hydrogen atom or a methyl group. A represents a group selected from an alkoxy group having 1 to 22 carbon atoms and an aryloxy group having 6 to 20 carbon atoms. B represents a group having an unsaturated bond represented by the following formula (1).

(1)

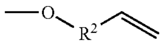

In the formula, $R^2$ represents a single bond, or a substituted or unsubstituted divalent hydrocarbon group having 1 to 20 carbon atoms and optionally containing an oxygen atom at a position not adjacent to any oxygen in the formula (1).

C represents a group having a linear organopolysiloxane structure represented by the following formula (2), or a group having a dendritic organopolysiloxane structure represented by the following (3-1) or (3-2).

(2)

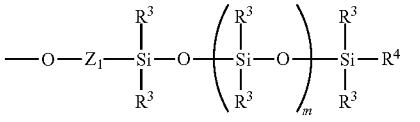

In the formula (2), $Z_1$ represents a divalent organic group, $R^3$'s each independently represent a saturated hydrocarbon group having 1 to 10 carbon atoms or a phenyl group, $R^4$ represents a saturated hydrocarbon group having 1 to 10 carbon atoms, and "m" represents an integer of 0 to 100.

(3-1)

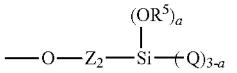

(3-2)

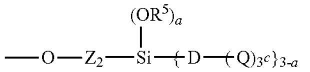

In the formulae (3-1) and (3-2), $Z_2$ represents a divalent organic group, "a" represents a number of 0 to 3, Q represents a group represented by the following formula (3), D represents an organopolysiloxanyl group having a dendritic structure with a hierarchical number of "c" and a valence of $3^c+1$, that is "3 to the $c^{th}$ power"+1, and "c" represents an integer of 1 to 8.

(3)

Q: 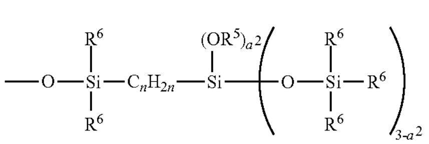

$R^5$ represents a saturated hydrocarbon group having 1 to 10 carbon atoms or a phenyl group, $R^6$ represents a saturated hydrocarbon group having 1 to 8 carbon atoms or a phenyl group, $R^7$ represents a hydrogen atom, a saturated hydrocarbon group having 1 to 10 carbon atoms, or a phenyl group, $a^2$ represents a real number of 0 to 2, and "n" represents an integer of 2 to 12.

An order of bonding of the repeating units represented by the formulae (I), (II), and (III) is not limited. "q" and "r" are not 0, and "p", "q" and "r" represent integers and are such numbers that the polymer crosslinking agent has a number-average molecular weight of 1,000 to 1,000,000 g/mol.

$$M_xD_yT_zQ_w \quad (4)$$

In the formula, M represents a siloxane unit of $R^8{}_3SiO_{1/2}$, D represents a siloxane unit of $R^8{}_2SiO_{2/2}$, T represents a siloxane unit of $R^8SiO_{3/2}$, and Q represents a siloxane unit of $SiO_{4/2}$; $R^8$'s each independently represent a hydrogen atom, a substituted or unsubstituted alkyl group having 1 to 10 carbon atoms, or a substituted or unsubstituted aryl group having 6 to 22 carbon atoms; at least two of the siloxane units contain hydrogen atoms; "x", "y", "z", and "w" each represent 0 or a positive number, provided that $y+z+w \geq 1$, and are such numbers that the organoohydrogen polysiloxane represented by the general formula (4) has a number-average molecular weight of 500 to 900,000 g/mol; and an order of bonding of the siloxane units represented by M, D, T, and Q is not limited.

Hereinafter, the present invention will be described in detail, but the present invention is not limited thereto. Incidentally, the term "(meth)acryl" used in the following description refers to methacryl and acryl. The same is also applied to the term "(meth)acrylate", and this similarly refers to methacrylate and acrylate.

In the present invention, the number-average molecular weight refers to a number average molecular weight measured by gel permeation chromatography (GPC) under the following conditions using polystyrene as a standard substance. Moreover, in the present invention, polydispersity (Mw/Mn) is calculated by dividing a value of the weight-average molecular weight measured under the same conditions for number-average molecular weight as mentioned above by a value of the number-average molecular weight.

[Measurement Conditions]

Developing solvent: tetrahydrofuran (THF)

Flow amount: 0.6 mL/min

Detector: Differential refractive index detector (RI)

Column: TSK Guard column SuperH-H

TSKgel SuperHM-N (6.0 mm I.D.×15 cm×1)

TSKgel SuperH2500 (6.0 mm I.D.×15 cm×1) (each available from Tosoh Corporation)

Column temperature: 40° C.

Sample injection amount: 50 μL (THF solution with a concentration of 0.3% by mass)

The present invention provides a cosmetic containing a high molecular weight polymer obtained by addition polymerization between: a polymer crosslinking agent which is a (meth)acrylic-based graft silicone having a main chain with (meth)acrylic-based repeating units and side chains with unsaturated bonds and an organopolysiloxane structure; and an organohydrogen polysiloxane. From the viewpoint of storage stability, the high molecular weight polymer is preferably swollen with a liquid oil agent in advance. In this event, the liquid oil agent is preferably an ester oil.

Besides the liquid oil agent for swelling the high molecular weight polymer, the inventive cosmetic preferably further contains an oily component. This oily component is one normally employed for cosmetics, and may be an oil mixture of two or more kinds, and any oily component in a solid, semi-solid, or liquid state can be used. A liquid oily component is preferable.

Further, the inventive cosmetic can be in a form of emulsion by blending water therewith.

Furthermore, the inventive cosmetic can be blended with an optional component as necessary. Examples of such optional components include, but are not particularly limited to, components normally used for cosmetics, such as ultraviolet absorbers, ultraviolet absorbing-scattering agents, compounds having alcoholic hydroxyl group, water-soluble or water-swelling polymers, powders, surfactants, oily thickeners, oily film-forming agents, preservatives, antioxidants, pH adjusters, chelating agents, cooling agents, anti-inflammatory agents, other agents, etc.

High Molecular Weight Polymer

The high molecular weight polymer used in the present invention can be obtained by addition polymerization of: a (meth)acrylic-based graft silicone having a main chain with (meth)acrylic-based repeating units represented by the following formulae (I), (II), and (III), and side chains with unsaturated bonds and an organopolysiloxane structure as a polymer crosslinking agent; and an organohydrogen polysiloxane represented by the following general formula (4).

(I)

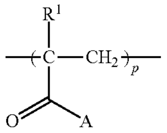

(II)

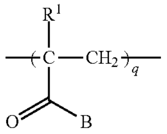

(III)

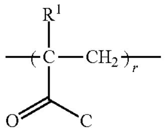

In the formulae, $R^1$'s are each independently a hydrogen atom or a methyl group. Particularly, a methyl group is preferable because the reaction is easily controlled in synthesizing the crosslinking agent. A is a group selected from alkoxy groups having 1 to 22 carbon atoms and aryloxy groups having 6 to 20 carbon atoms. Examples of the alkoxy groups include aliphatic alkoxy groups, such as a methoxy group, an ethoxy group, an n-propoxy group, an isopropoxy group, an n-butoxy group, an i-butoxy group, a t-butoxy group, an isopentyloxy group, an n-hexyloxy group, a 2-ethylhexyloxy group, a 3,5,5-trimethyl-1-hexyloxy group, a nonanyloxy group, an isodecyloxy group, a 2-propylheptyloxy group, a 2-isopropyl-5-methylhexyloxy group, a lauryloxy group, a tridecyloxy group, a heptadecyloxy group, a stearyloxy group, a heneicosanyloxy group, and a behenyloxy group; alicyclic alkoxy groups, such as a cyclohexyloxy group and an isobornyloxy group; etc. The examples further include alkoxyalkoxy groups, such as a methoxymethoxy group, a 2-ethoxyethoxy group, a 1-ethoxybutoxy group, and a 2-butoxyethoxy group. Examples of the aryloxy groups include a phenoxy group, a benzyloxy group, a tolyloxy group, etc. Among these, from the viewpoint of affinity for ester oil, an alkoxy group having 1 to 20 carbon atoms is preferable, and an alkoxy group having 4 to 18 carbon atoms is more preferable.

B is a group having an unsaturated bond represented by the following formula (1). From the viewpoint of the reaction rate of the addition polymerization, B is preferably an allyloxy group, a 2-allyloxyethoxy group, more preferably a 2-allyloxyethoxy group.

(1)

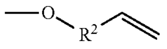

In the formula, $R^2$ is a single bond, or a substituted or unsubstituted divalent hydrocarbon group having 1 to 20 carbon atoms and optionally containing an oxygen atom at a position not adjacent to any oxygen in the formula (1).

C is a group having a linear organopolysiloxane structure represented by the following formula (2), or a group having a dendritic organopolysiloxane structure represented by the following (3-1) or (3-2). Among these, C is preferably a group having a linear organopolysiloxane structure represented by the following formula (2).

(Linear Organopolysiloxane Group)

(2)

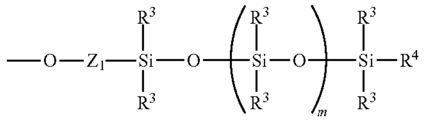

In the formula (2), $Z_1$ represents a divalent organic group. $R^3$'s each independently represent a saturated hydrocarbon group having 1 to 10 carbon atoms or a phenyl group. $R^4$ represents a saturated hydrocarbon group having 1 to 10 carbon atoms. "m" represents an integer of 0 to 100.

In the formula (2), $Z_1$ is a divalent organic group, preferably a divalent saturated hydrocarbon group having 2 to 12 carbon atoms, further preferably a propylene group. $R^3$ is a saturated hydrocarbon group having 1 to 10 carbon atoms or a phenyl group, preferably a saturated hydrocarbon group having 1 to 5 carbon atoms, further preferably a methyl group. $R^4$ is a saturated hydrocarbon group having 1 to 10 carbon atoms, preferably a saturated hydrocarbon group having 1 to 5 carbon atoms, further preferably a methyl group. "m" is an integer of 0 to 100, preferably an integer of 1 to 60, further preferably an integer of 5 to 30.

(Dendritic Organopolysiloxane Group)

(3-1)

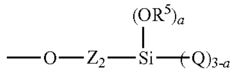

(3-2)

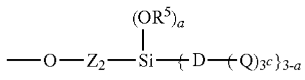

In the formulae (3-1) and (3-2), $Z_2$ represents a divalent organic group. "a" represents a number of 0 to 3. Q represents a group represented by the following formula (3). D represents an organopolysiloxanyl group having a dendritic structure with a hierarchical number of "c" and a valence of $3^c+1$, that is, "3 to the $c^{th}$ power"+1. "c" represents an integer of 1 to 8.

(3)

Q: 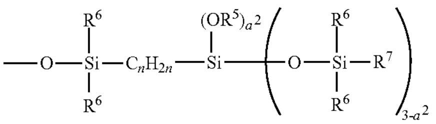

$R^5$ represents a saturated hydrocarbon group having 1 to 10 carbon atoms or a phenyl group. $R^6$ represents a saturated hydrocarbon group having 1 to 8 carbon atoms or a phenyl group. $R^7$ represents a hydrogen atom, a saturated hydrocarbon group having 1 to 10 carbon atoms, or a phenyl group. $a^2$ represents a real number of 0 to 2. "n" represents an integer of 2 to 12.

In the formulae (3-1) and (3-2), $R^5$ is a saturated hydrocarbon group having 1 to 10 carbon atoms or a phenyl group, preferably a saturated hydrocarbon group having 1 to 5 carbon atoms, further preferably a methyl group. $R^6$ is a saturated hydrocarbon group having 1 to 8 carbon atoms or a phenyl group, preferably a saturated hydrocarbon group having 1 to 6 carbon atoms, more preferably a saturated hydrocarbon group having 1 to 3 carbon atoms, further preferably a methyl group. $Z_2$ is a divalent organic group, preferably a saturated hydrocarbon group having 1 to 10 carbon atoms, further preferably a saturated hydrocarbon having 1 to 5 carbon atoms. D is an organopolysiloxanyl group having a dendritic structure with a hierarchical number of "c" and a valence of $3^c$+1 (i.e., "3 to the $c^{th}$ power"+1). "c" is an integer of 1 to 8, preferably an integer of 1 to 4, further preferably an integer of 1 to 2.

In detail, the group represented by the formula (3-1) or (3-2) is represented by the following structures.

(3-1')

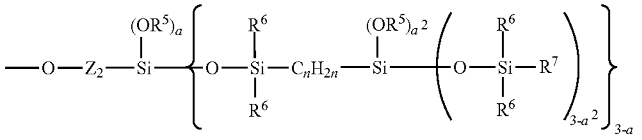

(3-2')

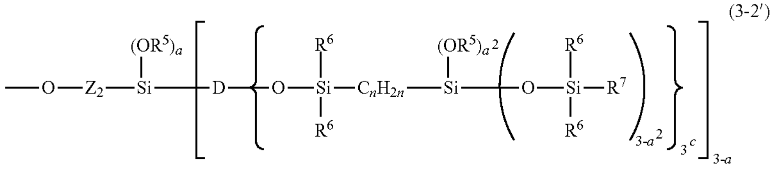

In the formula (3-2'), D is represented by, for example, the following structure.

When the hierarchical number (c) of D is 1

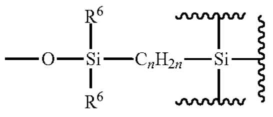

When the heirarchical number (c) of D is 1

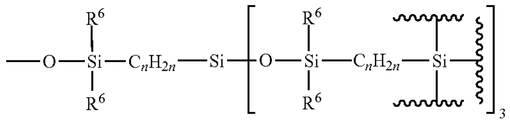

When the heirarchical number (c) of D is 2

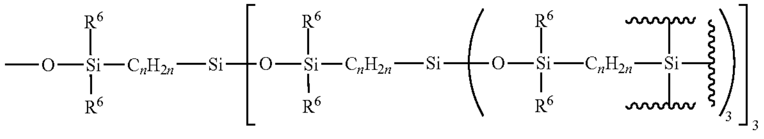

When the heirarchical number (c) of D is 3

Examples of the group represented by C in the formula (III) include the following structures.

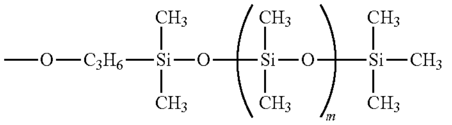

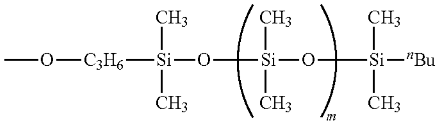

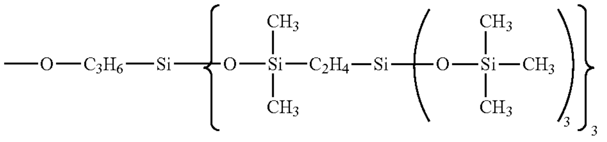

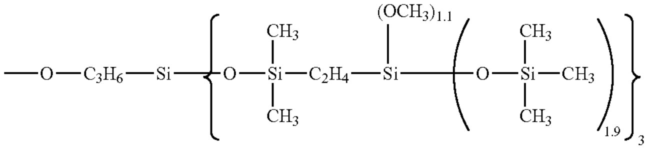

-continued

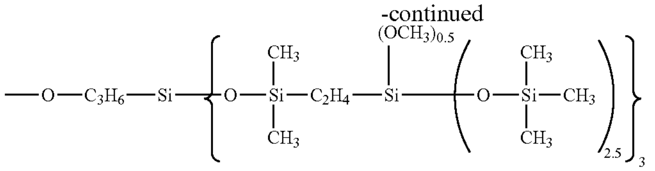

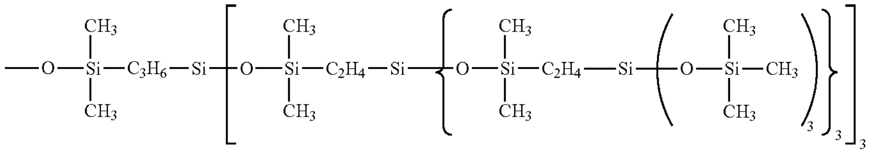

Structure in which the hierarchical number of D is 1

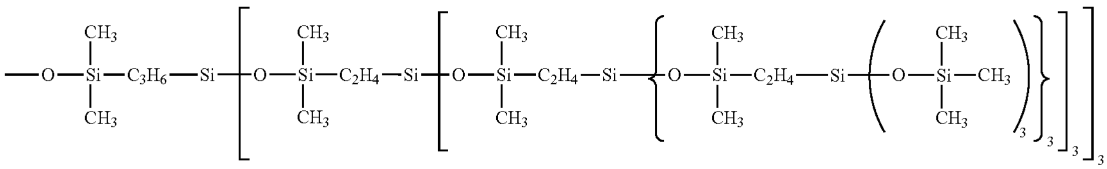

Structure in which the hierarchical number of D is 2

The order of bonding of the repeating units represented by the formulae (I), (II), and (III) is not limited, and the arrangement constituted by these repeating units may be irregular, or may be regular. The repeating units (I), (II) an (III) may each be constituted by at least one kind, or may be constituted by multiple types. In the formulae, "p", "q" and "r" are integers, "q" and "r" are not 0, preferably "q" is 2 or more, more preferably 2 to 10, and "r" is preferably 1 or more, more preferably 1 to 20. "p", "q" and "r" are such numbers that the polymer crosslinking agent has a number-average molecular weight of 1,000 to 1,000,000 g/mol, preferably 3,000 to 100,000 g/mol, further preferably 5,000 to 50,000 g/mol.

Hereinafter, a polymerization method of the polymer crosslinking agent will be described in detail. The polymerization method of the polymer crosslinking agent of the present invention is not particularly limited. The polymer crosslinking agent can be obtained, for example, by subjecting monomers represented by the following general formulae (5), (6), and (7) to group transfer polymerization.

(5)

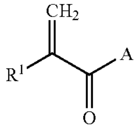

(6)

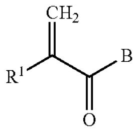

-continued (7)

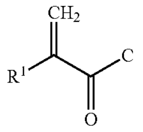

In the formulae, $R^1$, A, B, and C are as defined above.

Examples of the compound represented by the general formula (5) include, but are not limited to, the following compounds:

methyl(meth)acrylate, ethyl (meth)acrylate, n-butyl (meth)acrylate, isobutyl (meth)acrylate, t-butyl (meth)acrylate, n-hexyl (meth)acrylate, isopentyl (meth)acrylate, lauryl (meth)acrylate, 2-ethylhexyi (meth)acrylate, stearyl (meth) acrylate, cyclohexyl (meth)acrylate, behenyl (meth)acrylate, isodecyl (meth)acrylate, 2-propylheptyl (meth)acrylate, 3,5,5-trimethyl-1-hexyl (meth)acrylate, nonanyl (meth)acrylate, 2-propylheptyl (meth)acrylate, 2-isopropyl-5-methylhexyl (meth)acrylate, tridecyl (meth)acrylate, heptadecyl (meth) acrylate, heneicosanyl (meth)acrylate, isobornyl (meth) acrylate, 2-butoxyethyl (meth)acrylate, 2-ethoxyethyl (meth)acrylate, and 1-ethoxybutyl (meth)acrylate.

Examples of the compound represented by the general formula (6) include, but are not limited to, the following compounds:

vinyl (meth)acrylate, allyl (meth)acrylate, and 2-allyloxyethyl (meth)acrylate.

Examples of the compound represented by the general formula (7) include, but are not limited to, the following compounds:

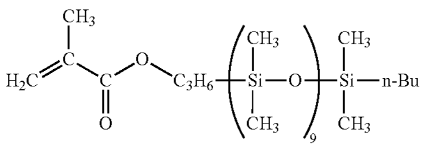
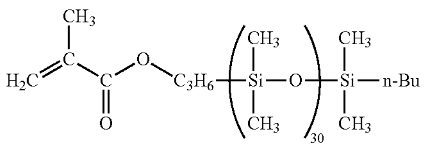
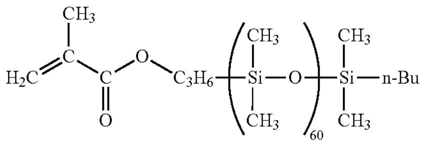
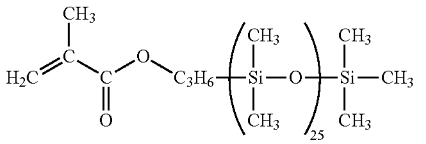
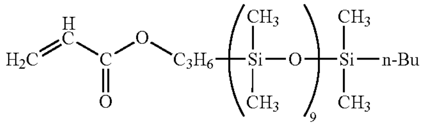
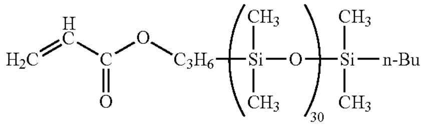
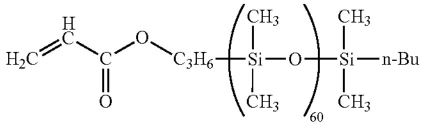
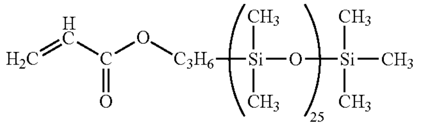
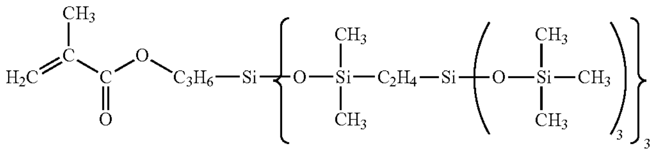
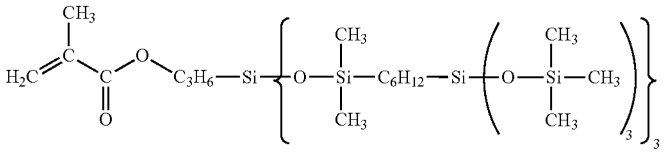
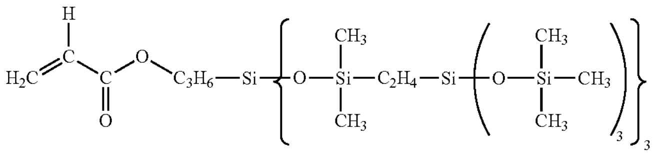
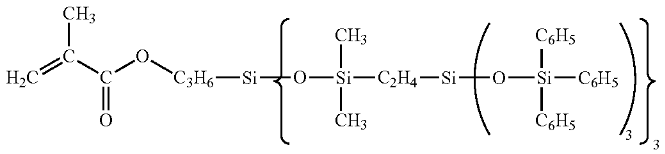
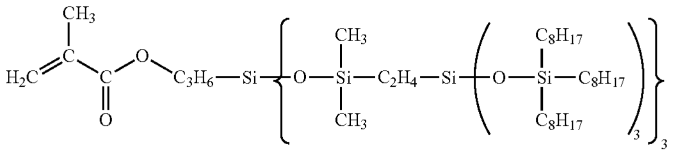
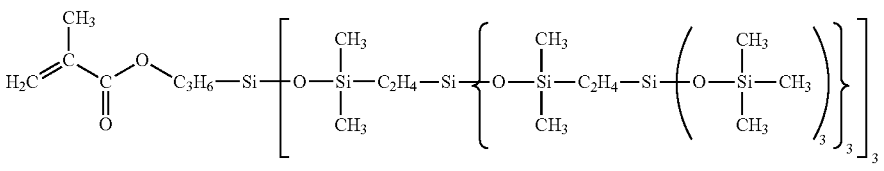
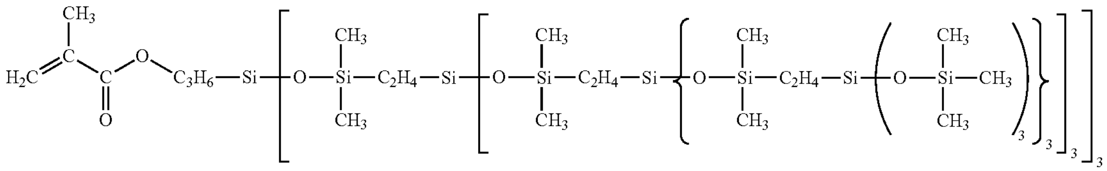

-continued

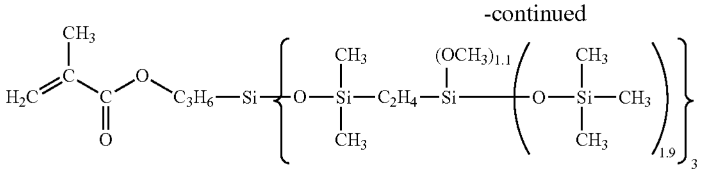

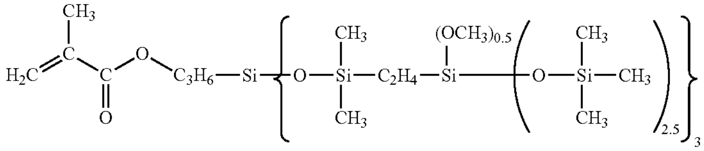

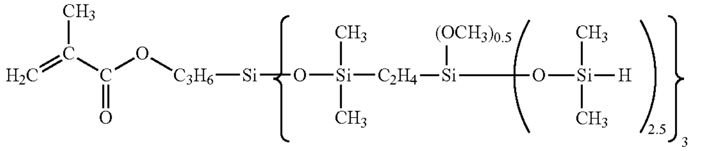

Hereinafter, a producing method by the group transfer polymerization is exemplified, but as the producing method, other polymerization methods may be used, and it is not limited to the following method.

A three-necked flask sufficiently dried is charged with a catalyst, and a solvent is added thereto. Further, an initiator is added thereto and mixed. Then, monomers (5), (6) and (7) are added dropwise to the mixture using a dropping funnel and the resulting mixture is stirred. The reaction solution is cooled depending on the degree of heat generation and maintained at an appropriate temperature. After the dropwise addition, stirring is continued until the monomers are consumed, and a reaction terminator is added thereto to complete the reaction. After the reaction, washing with water is carried out, if necessary, and the solvent is distilled off under reduced pressure.

As the order of adding a catalyst, a solvent, an initiator and monomers of the group transfer polymerization, an appropriate order can be selected depending on the cases. For example, the reaction may be carried out by previously mixing monomers (5), (6) and (7), a solvent and an initiator to prepare a solution, and finally adding a catalyst thereto.

In a case where all the monomers used for the reaction are previously mixed and added dropwise, a random copolymer can be synthesized. Also, when each monomer used for the reaction is alternately added, a block copolymer can be synthesized.

As an initiator, the following compounds can be used, but the initiators which can be used in the present invention are not limited to the initiators exemplified below.

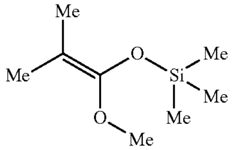

Dimethylketene methyl trimethylsilyl acetal

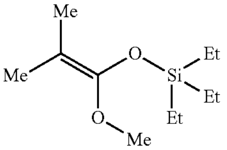

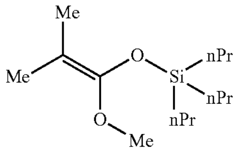

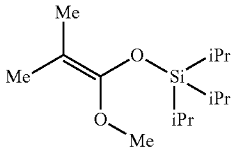

-continued

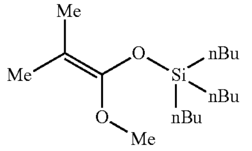

In the formulae, Me represents a methyl group, Et represents an ethyl group, nPr represents an n-propyl group, iPr represents an isopropyl group, and nBu represents an n-butyl group.

As a reaction solvent, an aprotonic organic solvent may be used. Examples thereof include ethyl acetate, propionitrile, toluene, xylene, bromobenzene, dimethoxyethane, diethoxyethane, diethyl ether, tetramethylenesulfone, N,N-dimethylformamide, N,N-dimethylacetamide, N-methylpyrrolidone, anisole, 2-butoxyethoxytrimethylsilane, cellosolve acetate, crown ether, acetonitrile and tetrahydrofuran (hereinafter may also referred to as THF). From the viewpoint of reaction efficiency, preferable are dichloromethane, toluene, acetonitrile, and tetrahydrofuran, and further preferable is tetrahydrofuran.

The reaction temperature is preferably −100° C. to 150° C., more preferably 0° C. to 50° C., further preferably 10° C. to 30° C.

The temperature in the distillation under reduced pressure is preferably 80° C. to 300° C., more preferably 100° C. to 200° C., further preferably 120° C. to 180° C. In addition, the pressure in this event is preferably 1013 hPa or less, more preferably 101.3 hPa or less, further preferably 1.013 hPa or less.

As the catalyst, one selected from an anionic catalyst, a Lewis acid catalyst and an organocatalyst can be used, which have been generally known as a catalyst for the group transfer polymerization.

Anionic Catalyst

For example, there may be mentioned tris(dimethylamino)sulfonium difluorotrimethylsilicate, tris(dimethylamino)sulfonium cyanide, tetraphenylarsonium cyanide, tris(dimethylamino)sulfonium azide, tetraethylammonium azide, bis(dialkylaluminum) oxide, boron trifluoride etherate, alkali metal fluoride, alkali metal cyanide, alkali metal azide, tris(dimethylamino)sulfonium difluorotriphenyl stannate, tetrabutylammonium fluoride, tetramethylammonium fluoride, tetraethylammonium cyanide, tetrabutylammonium benzoate, tetrabutylammonium bibenzoate and tetrabutylammonium m-chlorobenzoate.

Lewis Acid Catalyst

For example, there may be mentioned zinc iodide, zinc bromide, zinc chloride, mono- and dialkylaluminum halide and dialkylaluminum oxide.

Organocatalyst

For example, there may be mentioned 1,3-diisopropyl-4,5-dimethylimidazol-2-ylidene, 1,3-diisopropylimidazol-2-ylidene, 1,3-di-t-butylimidazol-2-ylidene, 1,8-diazabicyclo[5.4.0]-7-undecene, 2,8,9-trimethyl-2,5,8,9-tetraaza-1-phosphabicyclo[3.3.3]undecane, 2,8,9-triisobutyl-2,5,8,9-tetraaza-1-phosphabicyclo[3.3.3]undecane, 1-t-butyl-2,2,4,4,4-pentakis(dimethylamino)-2λ$^5$,4λ$^5$-catenadi(phosphazene), 1-t-butyl-4,4,4-tris(dimethylamino)-2,2-bis[tris(dimethylamino)-phosphoranylideneamino]-2λ$^5$,4λ$^5$-catenadi(phosphazene), tris(2,4,6-trimethoxyphenyl)phosphine, tris-(pentafluorophenyl)borane, triethylsilyl trifluoromethanesulfonate, triphenylcarbenium tetrakis-(pentafluorophenyl)borate, trifluoromethanesulfonimide and 1-[bis(trifluoromethanesulfonyl)methyl]-2,3,4,5,6-pentafluorobenzene.

As the reaction terminator, a compound which can donate a proton is used. Examples thereof include methanol, isopropyl alcohol, n-butyl alcohol and water.

The polymer crosslinking agent becomes a high molecular weight polymer by addition polymerization with an organohydrogen polysiloxane represented by the following general formula (4). This high molecular weight polymer can swell by incorporating a liquid oil agent which has the same mass or more as its own mass of the high molecular weight polymer.

$$M_xD_yT_zQ_w \quad (4)$$

In the formula, M represents a siloxane unit of $R^8{}_3SiO_{1/2}$, D represents a siloxane unit of $R^8{}_2SiO_{2/2}$, T represents a siloxane unit of $R^8SiO_{3/2}$, and Q represents a siloxane unit of $SiO_{4/2}$. $R^8$'s each independently represent a hydrogen atom, a substituted or unsubstituted alkyl group having 1 to 10 carbon atoms, or a substituted or unsubstituted aryl group having 6 to 22 carbon atoms. At least two of the siloxane units contain hydrogen atoms. $R^8$ is preferably a hydrogen atom, an alkyl group having 1 to 4 carbon atoms, or an aryl group having 6 to 12 carbon atoms, further preferably a hydrogen atom, a methyl group, or a phenyl group. Such functional groups enhance the affinity of the resulting high molecular weight polymer for ester oil.

“x”, “y”, “z”, and “w” each represent 0 or a positive number, provided that $y+z+w \geq 1$. “z” and “w” are each preferably 10 or less, further preferably 0. “z” and “w” within this range are preferable because the organohydrogen polysiloxane becomes linear with less branches, and the reaction with the polymer crosslinking agent results in more uniform high molecular weight polymer.

The number of hydrosilyl groups (SiH groups) in a molecule of the organohydrogen polysiloxane is 2 or more, preferably 2 to 3. More preferably, only the M unit in the general formula (4) has hydrosilyl groups. If the number is less than 2, there are so few crosslinking points that swelling owing to a liquid oil agent may not occur sometimes.

The organohydrogen polysiloxane represented by the general formula (4) has a number-average molecular weight of 500 to 900,000 g/mol, preferably 500 to 100,000 g/mol, further preferably 500 to 50,000 g/mol. If the number-average molecular weight is outside these ranges, the resulting high molecular weight polymer might have poor affinity for liquid oil agent. The order of bonding the siloxane units represented by M, D, T, and Q is not limited.

Moreover, the organohydrogen polysiloxane represented by the general formula (4) has a polydispersity (Mw/Mn) of preferably 1.0 to 2.5, more preferably 1.2 to 1.8. The polydispersity is preferably within these ranges because the inside of the crosslinked product becomes uniform and swelling with a liquid oil agent is facilitated.

To obtain the high molecular weight polymer of the present invention, the above-described polymer crosslinking agent and organohydrogen polysiloxane are allowed to react in the presence of a platinum compound (for example, chloroplatinic acid, alcohol-modified chloroplatinic acid, chloroplatinic acid-vinyl siloxane complex, etc.), or a rhodium compound, at room temperature or under heating (about 50 to 120° C.). At the time of the reaction, it may be carried out without a solvent, or an organic solvent may be used, if necessary. Examples of the organic solvent include aliphatic alcohol-based solvents, such as methanol, ethanol, 2-propanol, and butanol; aromatic hydrocarbon-based solvents, such as benzene, toluene, and xylene; aliphatic or alicyclic hydrocarbon-based solvents, such as n-pentane, n-hexane, and cyclohexane; halogenated hydrocarbon-based solvents, such as dichloromethane, chloroform, and carbon tetrachloride; ketone-based solvents, such as acetone and methyl ethyl ketone; silicone oils, such as decamethylcyclopentasiloxane; ester oils, such as glyceryl triisooctanoate (triethylhexanoin), neopentyl glycol diethylhexanoate, and isopropyl myristate; etc. Since the high molecular weight polymer of the present invention is excellent in affinity for ester oil, in the case where the obtained high molecular weight polymer is supposedly swollen with an ester oil, the reaction is particularly preferably without a solvent or using an ester oil as the solvent.

In order to obtain a composition in which the high molecular weight polymer is swollen with a liquid oil agent, it can be obtained by: first synthesizing the high molecular weight polymer alone; then purifying the same; subsequently mixing a liquid oil agent therewith; and kneading the mixture. Alternatively, it can be also obtained by; subjecting the polymerized product which still contains the organic solvent used for the reaction to a purification treatment; then, removing the solvent and volatile components such as odorous components; mixing a liquid oil agent; and kneading the resulting mixture. Meanwhile, the purification treatment may be carried out after the high molecular weight polymer is mixed with the liquid oil agent.

The purification treatment is carried out as necessary. For example, it is preferably carried out by adding water or an acidic substance selected from an organic acid or an inorganic acid and a salt thereof. Although it is possible to carry out the treatment with water alone without adding the acidic substance, it is preferable to carry out the treatment by adding the acidic substance to control the reaction in a constant level. Also, an amount of the acidic substance to be added at this time is preferably 0.01 to 10 parts by mass, more preferably 0.02 to 5 parts by mass, based on 100 parts by mass of the high molecular weight polymer. When the amount is within the above-mentioned ranges, the deodorizing effect is high, and the neutralized salt does not precipitate in the composition after the purification treatment. Meanwhile, these organic acids may be added as such, but are preferably added as a 1 to 50 mass % aqueous solution. However, even if an aqueous organic acid solution is added to the polymerized product containing no liquid oil agent, the contacting efficiency with a treatment liquid is so low that it is difficult to increase the degree of purification and to carry out the neutralization reaction. The purification treatment is preferably carried out by adding the aqueous solution in an amount of 5 to 30 parts by mass based on 100 parts by mass of the high molecular weight polymer from the viewpoint of contacting efficiency. A pH of the aqueous solution of the acidic substance is preferably set to be 2 to 5. The pH within this range is preferable because reactions such as cleavage of the siloxane chain do not occur. The pH is more preferably 3 to 5.

As the treatment condition after the addition of the acidic substance, the reaction may be carried out without heating, but it is preferable to perform heating to 20 to 150° C., particularly preferably to 50 to 100° C. After addition of the acidic substance, it is preferable to neutralize the resulting mixture with a basic neutralizing agent. The basic neutralizing agent may be added as it is, but it is preferable to add it as a 1 to 50 mass % aqueous solution. Also, an amount thereof to be added is adjusted such that the functional group equivalent of the acidic substance and the basic neutralizing agent is preferably 1/0.1 to 0.1/1, more preferably 1/0.3 to 0.3/1, and that the pH after neutralization is 5 to 8.

After addition of the basic neutralizing agent, it is preferable to carry out a heat treatment at 20 to 150° C., more preferably at 20 to 80° C., as the treatment condition.

Specific examples of the acidic substance include citric acid, lactic acid, tartaric acid, malic acid, glutamic acid, acetic acid, glycine, potassium dihydrogen phosphate, succinic acid, etc.; particularly preferably, citric acid, lactic acid and glutamic acid. Specific examples of the basic neutralizing agent include sodium carbonate, sodium hydrogen carbonate, sodium hydroxide, potassium hydroxide, disodium hydrogen phosphate, sodium acetate, etc.; particularly preferably, sodium carbonate, sodium hydrogen carbonate, sodium hydroxide.

These acidic substance and basic neutralizing agent are preferably selected from combinations by which a salt formed by neutralization has an effect as a pH buffering agent. In this manner, it is possible to not only reduce odor of the high molecular weight polymer but also obtain the effect of stabilizing the pH of the composition. Also, the high molecular weight polymer of the present invention can swell by incorporating a liquid oil agent whose mass is equal to or more than its own mass of the high molecular weight polymer. This confirmation is carried out as follows. The high molecular weight polymer and a liquid oil agent are mixed in the same mass and the mixture is left to stand at room temperature. After left to stand, the sample is placed on a net having a 100 mesh and left to stand for 5 minutes to confirm that no separation of the liquid oil agent is observed (the sample passes through the net).

For producing the composition of the present invention, the high molecular weight polymer and the liquid oil agent may be kneaded with a usual stirring machine. It is preferable to knead the materials under a shearing force. This is because the high molecular weight polymer has a three-dimensional crosslinked structure that does not dissolve in a solvent, so by providing sufficient dispersibility to the high molecular weight polymer and the liquid oil agent, a composition having a smooth appearance can be obtained.

The kneading treatment can be carried out, for example, with a three-roll mill, a two-roll mill, a side grinder, a colloid mill, a Gaulin homogenizer, a disper, etc. A method with a three-roll or a disper is preferable.

The inventive cosmetic can contain the following components as necessary.

Liquid Oil Agent

As the liquid oil agent to be used in the present invention, those which exhibit fluidity at 25° C. can be suitably used. From the viewpoint of usability, a liquid oil agent having a kinematic viscosity at 25° C. of 1 to 10,000 $mm^2/s$ is preferably used. Examples of such a liquid oil agent can include silicone oil, hydrocarbon oil, ester oil, higher fatty acid, higher alcohol, natural animal or vegetable oil, semi-synthetic oil, etc. The high molecular weight polymer and the liquid oil agent can be mixed as described above.

Examples of the silicone oil include organopolysiloxanes which are in a liquid state at normal temperature with low to high viscosity, such as dimethylpolysiloxane, methylphenylpolysiloxane, methylhydrogen polysiloxane, and dimethylsiloxanemethylphenylsiloxane copolymers; cyclic siloxanes, such as octamethylcyclotetrasiloxane (D4), decamethylcyclopentasiloxane (D5), dodecamethylcyclohexasiloxane (D6), tetramethyltetrahydrogen cyclotetrasiloxane (H4), and tetramethyltetraphenylcyclotetrasiloxane; branched siloxanes, such as tristrimethylsiloxysilane (M3T), tetrakistrimethylsiloxysilane (M4Q), and tristrimethylsiloxyphenylsilane; higher alkoxy-modified silicones, such as stearoxysilicone; alkyl-modified silicones; amino-modified silicones; fluorine-modified silicones; etc.

Examples of the hydrocarbon oil include chain and cyclic hydrocarbon oils. However, ones which are solid at normal temperature such as ceresin or Vaseline, are not preferable in view of usability. Specific examples include α-olefin oligomer, light isoparaffin, light liquid isoparaffin, squalane, synthetic squalane, vegetable squalane, squalene, liquid paraffin, liquid isoparaffin, etc.

Examples of the ester oil include diisobutyl adipate, 2-hexyldecyl adipate, di-2-heptylundecyl adipate, glycol distearate, isocetyl isostearate, trimethylolpropane triisostearate, ethylene glycol di-2-ethylhexanoate, neopentyl glycol diethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dioctanoate, neopentyl glycol dicaprate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isononyl isononanoate, isotridecyl isononanoate, isopropyl palmitate, 2-ethylhexyl palmitate, 2-hexyldecyl palmitate, 2-heptylundecyl palmitate, cholesteryl 12-hydroxystearate, dipentaerythritol fatty acid ester, isopropyl myristate, octyldodecyl myristate, 2-hexyldecyl myristate, myristyl myristate, hexyldecyl dimethyloctanoate, ethyl laurate, hexyl laurate, N-lauroyl-L-glutamic acid-2-octyldodecyl ester, diisostearyl malate, etc.

Also, examples of the ester oils that fall within the category of glyceride oil include acetoglyceryl, glyceryl triisooctanoate (triethylhexanoin), glyceryl triisostearate, glyceryl triisopalmitate, glyceryl monostearate, glyceryl di-2-heptylundecanoate, glyceryl trimyristate, diglyceryl isostearate myristate, etc.

Examples of the higher fatty acid include undecylenic acid, oleic acid, linoleic acid, linolenic acid, arachidonic acid, eicosapentaenoic acid (EPA), docosahexaenoic acid (DHA), isostearic acid, etc. Examples of the higher alcohol include oleyl alcohol, isostearyl alcohol, hexyldecanol, octyldodecanol, cetostearyl alcohol, 2-decyltetradecinol, monooleyl glyceryl ether (selachyl alcohol), etc.

Also, examples of the natural animal or vegetable oil agent and semi-synthetic oil agent include avocado oil, almond oil, olive oil, liver oil, beef leg oil, apricot kernel oil, wheat germ oil, sesame oil, rice germ oil, rice bran oil, Camellia sasanqua oil, safflower oil, cinnamon oil, squalene, squalene, turtle oil, soybean oil, teaseed oil, camellia oil, evening primrose oil, corn oil, rapeseed oil, Japanese tung oil, germ oil, persic oil, castor oil, castor oil fatty acid methyl ester, sunflower oil, grape oil, jojoba oil, macadamia nut oil, mink oil, meadowfoam oil, cottonseed oil, coconut fatty acid triglyceride, peanut oil, liquid lanolin, acetylated lanolin alcohol, lanolin fatty acid polyethylene glycol, egg yolk oil, etc.

Water

The inventive cosmetic can be blended with water according to the purpose. Blending water into the inventive cosmetic according to the usage in this manner makes the cosmetic more excellent in usability. The amount of water blended is suitably within a range of 95 mass % or less of the whole cosmetic. Moreover, the inventive cosmetic containing water can be in the form of emulsion.

Ultraviolet Absorbing Components

The inventive cosmetic may further contain one or two or more kinds of ultraviolet absorbing component. This makes the inventive cosmetic not only have favorable feeling on use and excellent usability and persistency, but also capable of absorbing ultraviolet ray. The ultraviolet absorbing component includes ultraviolet absorbers and ultraviolet scattering agents. Examples of the ultraviolet absorber include benzoic acid ultraviolet absorbers, such as para-amino benzoic acid; anthranilic acid-based ultraviolet absorbers, such as methyl anthranilate; salicylic acid-based ultraviolet absorbers, such as methyl salicylate; cinnamic acid-based ultraviolet absorbers, such as octyl para-methoxycinnamate; benzophenone-based ultraviolet absorbers, such as 2,4-dihydroxybenzophenone; urocanic acid-based ultraviolet absorbers, such as ethyl urocanate; dibenzoylmethane-based ultraviolet absorbers, such as 4-t-butyl-4'-methoxy-dibenzoylmethane; etc. It is also possible to use silicone derivatives having an ultraviolet-absorbing functional group described above.

Examples of the ultraviolet absorbing-scattering agents include particles that absorb and scatter ultraviolet ray, such as titanium oxide microparticles, iron-containing titanium oxide microparticles, zinc oxide microparticles, cerium oxide microparticles, and composites thereof. Among these, cinnamic acid-based ultraviolet absorbers, dibenzoylmethane-based ultraviolet absorbers, titanium oxide, and zinc oxide are preferable.

Compounds Having Alcoholic Hydroxyl Group

Compounds having alcoholic hydroxyl group are used for moisturizing and refreshing purposes or as a preservative or solvent. Examples thereof include lower alcohols, such as ethanol and isopropanol; sugar alcohols such as sorbitol and maltose; polyhydric alcohols, such as butylene glycol, propylene glycol, dipropylene glycol, pentylene glycol, glycerin, ethylhexyl glycerin; etc. The amount of these compounds blended is suitably within a range of 0.1 to 30 mass % of the whole cosmetic.

Water-Soluble or Water-Swelling Polymers

The water-soluble or water-swelling polymers are used for adjusting feeling, such as viscosity adjustment, film formation, and moisturization of the cosmetic. Examples thereof include plant polymers, such as Arabia gum, tragacanth, galactan, guar gum, karaya gum, carrageenan, pectin, agar, quince seed (marmelo), starch (rice, corn, potato, wheat, and so on), algae colloid, and locust bean gum; microbial polymers, such as a xanthan gum, dextran, succinoglucan, and pullulan; animal polymers, such as collagen, casein, albumin, and gelatin; starch polymers, such as carboxymethyl starch and methyl hydroxypropyl starch; cellulose polymers, such as methyl cellulose, ethyl cellulose, methyl hydroxypropyl cellulose, carboxymethyl cellulose, hydroxymethyl cellulose, hydroxypropyl cellulose, nitrocellulose, and sodium carboxymethyl cellulose; polyethylene glycol polymers; alginic acid polymers, such as sodium alginate and propylene glycol alginate ester; film-forming agents, such as polyvinyl alcohol and polyvinyl pyrrolidone; vinyl polymers, such as carboxyvinyl polymer and (acrylates/alkyl acrylate (C10-30)) crosspolymer; acrylic polymers, such as sodium polyacrylate, (ammonium acryloyldimethyl taurate/VP) copolymer, sodium acryloyldimethyl taurate copolymer, (sodium acrylate/sodium acryloyldimethyl taurate) copolymer, (hydroxyethyl acrylate/sodium acryloyldimethyl taurate) copolymer, and polyacrylamide; and other synthetic water-soluble polymers, such as polyethyleneimine and cationic polymers. The amount of the water-soluble or water-swelling polymers blended is suitably within a range of 0.1 to 25 mass % of the whole cosmetic.

Powders

The powders may have any shape (spherical, needle-like, plate-like, etc.), particle size (fumed, microparticle, pigment-class, etc.), and particle structure (porous, non-porous, etc.). Examples thereof include inorganic powder, organic powder, metal soap, and colorant (e.g., inorganic pigments such as metal powder pigment, tar dye, natural dye, and pearl pigment), etc. These powder components may be surface-treated with a metal soap, silica, aluminum oxide, aluminum hydroxide or other by a known method or may be a composite powder to suppress the surface activity, enhance the dispersibility, and improve feeling when the cosmetic is applied.

Examples of the inorganic powder include titanium oxide, zinc oxide, barium sulfate, calcium sulfate, magnesium sulfate, calcium carbonate, magnesium carbonate, talc, mica, kaolin, sericite, muscovite, synthetic mica, phiogopite, lepidolite, biotite, lithia mica, silicic acid, anhydrous silicic acid, aluminum silicate, magnesium silicate, aluminum magnesium silicate, calcium silicate, barium silicate, strontium silicate, metal tungstate salt, hydroxy apatite, vermiculite, higilite, bentonite, montmorillonite, hectorite, zeolite, ceramic powder, dibasic calcium phosphate, alumina, aluminum hydroxide, boron nitride, boron nitride, silica, etc.

Examples of the organic powder include polyester powder, polyethylene powder, polystyrene powder, polyurethane powder, polymethylmethacrylate powder, methyl methacrylate crosspolymer, cellulose powder, silk powder, nylon powders, such as nylon 12 and nylon 6, fibrous powders thereof, crosslinked silicone fine powder having crosslinking structure from dimethylpolysiloxane, crosslinked spherical polymethylsilsesquioxane fine powder, fine powder obtained by coating the surface of crosslinked spherical organopolysilicone rubber with polymethylsilsesquioxane particles, resin laminated powder, starch powder, fatty acid starch derivative powder, lauroyl lysine, etc.

Examples of the metal soap include zinc stearate, aluminum stearate, calcium stearate, magnesium stearate, zinc myristate, magnesium myristate, etc.

Examples of the colorant include inorganic pigments, such as titanium oxide, iron oxide, titanium black, carbon black, chromium hydroxide, chromium oxide, Prussian blue, ultramarine blue, and aluminum powder; tar dyes, such as Red No. 226 and Yellow No. 4; natural dyes, such as carmine; pearl pigments, such as titanium mica, synthetic phlogopite, titanium mica coated with iron oxide, and synthetic phlogopite coated with titanium oxide; etc.

Further, these powders may be composite powders, or may be treated with, for example, general oil, silicone oil, fluorine compound, surfactant, reactive organohydrogen-polysiloxane, organopolysiloxane having a hydrolysable alkoxysilane group, or an acryl-silicone copolymer having hydrolysable silyl group for use. These powders may be used solely or in combination of two or more kinds.

Particularly, when an ON type cosmetic is prepared, it preferably contains (disperses therein) a surface-hydrophobized powder in the oil phase to reduce flowing down of the powder after the cosmetic is applied. This further enhances the adhesion to the skin and cosmetic durability. Specific examples of the powder are as described above. Especially, the surface-hydrophobized powder is preferably a hydrophobized pigment.

Additionally, the amount of these powders blended is suitably within a range of 0.1 to 99 mass % of the whole cosmetic. Particularly, in a case of powdery solid cosmetic, such powders are suitably blended in an amount ranging from 80 to 99 mass % of the whole cosmetic.

The powders may be blended to the inventive cosmetic directly, or may be used in such a state that the powders are dispersed in a dispersion medium in advance. Examples of the dispersion medium usable in this event are the same as the liquid oil agent described above. A dispersant may be used in the preparation of this dispersed material. Preferable examples of the dispersant that can be employed include acryl silicone KP-578 (available from Shin-Etsu Chemical Co., Ltd.), etc., besides generally-used dispersants for dispersing powder.

Surfactants

The inventive cosmetic may further contain one or two or more kinds of surfactant. Blending a surfactant according to the usage in this manner makes the inventive cosmetic more excellent in usability. The surfactant includes anionic, cationic, nonionic, and amphoteric surfactants. The inventive cosmetic can employ and contain, without particular limitation, any surfactant that is used for ordinal cosmetics.

Specific examples thereof are as follows. Examples of the anionic surfactant include fatty acid soap, such as sodium stearate and triethanolamine palmitate; alkyl ether carboxylic acids and salts thereof; condensation salts of amino acid and fatty acid; alkane sulfonate salts; alkene sulfonate salts; sulfonate salts of fatty acid esters, sulfonate salts of fatty acid amides; sulfonate salts of formalin condensate; alkyl sulfate ester salts; sulfate ester salts of secondary higher alcohols; sulfate ester salts of alkyl and allyl ethers; sulfate ester salts of fatty acid esters; sulfate ester salts of fatty acid alkylolamides; sulfate ester salts, such as Turkey red oil; alkyl phosphate salts; ether phosphate salts; alkyl allyl ether phosphate salts; amide phosphate salts; N-acyl lactate salt; N-acylsarcosine salts; N-acylamino acid-based activators; etc. Examples of the cationic surfactant include alkyl amine salts; amine salts of polyamines, amino alcohol fatty acid derivatives, etc.; alkyl quaternary ammonium salts, aromatic quaternary ammonium salts, pyridinium salts, imidazolium salts, etc.

Examples of the nonionic surfactant include sorbitan fatty acid esters, glycerin fatty acid esters, polyglycerin fatty acid esters, propylene glycol fatty acid esters, polyethylene glycol fatty acid esters, sucrose fatty acid esters, methyl glucoside fatty acid esters, alkyl polyglucosides, polyoxyethylene alkyl ethers, polyoxypropylene alkyl ethers, polyoxyethylene alkyl phenyl ethers, polyoxyethylene fatty acid esters, polyoxyethylene sorbitan fatty acid esters, polyoxyethylene sorbitol fatty acid esters, polyoxyethylene glycerin fatty acid esters, polyoxyethylene propylene glycol fatty acid esters, polyoxyethylene castor oil, polyoxyethylene hydrogenated castor oil, polyoxyethylene phytostanol ethers, polyoxyethylene phytosterol ethers, polyoxyethylene cholestanol ethers, and polyoxyethylene cholesterol ethers; linear or branched polyoxyalkylene-modified organopolysiloxanes, linear or branched organopolysiloxanes co-modified with polyoxyalkylene and alkyl, linear or branched polyglycerin-modified organopolysiloxanes, linear or branched organopolysiloxanes co-modified with polyglycerin and alkyl, alkanol amides, sugar ethers, sugar amides, etc.

Examples of the amphoteric surfactant include betaines, aminocarboxylic acid salts, imidazoline derivatives, amide amine type, etc.

Among these surfactants, preferable are linear or branched organopolysiloxanes having a polyoxyethylene chain in the molecule, linear or branched organopolysiloxanes having a polyglycerin chain in the molecule, or surfactants of these organopolysiloxanes co-modified with alkyl. Commercial products thereof are not particularly limited, but include KF-6011, KF-6011P, KF-6043, KF-6012, KF-6013, KF-6015, KF-6016, KF-6017, KF-6028, KF-6028P, KF-6038, KF-6100, KF-6104, KF-6105, and KF-6106 (these are available from Shin-Etsu Chemical Co., Ltd.); and the like. Moreover, the surfactant preferably has an HLB of 2 to 10, and is blended in an amount ranging from preferably 0.1 to 20 mass %, particularly suitably 0.2 to 10 mass %, of the whole cosmetic.

Oily Thickeners

Examples of the oily thickeners include particulate silica, such as silylated silica; organic modified clay minerals, such as disteardimonium hectorite; metal soaps, such as aluminum stearate; polysaccharide fatty acid esters, such as (palmitate/2-ethylhexanoate)dextrin and inulin stearate; sucrose fatty acid esters, such as sucrose acetate stearate; crosslinking organopolysiloxane; etc.

The crosslinking organopolysiloxane preferably swells by incorporating a liquid oil having a mass equal to or more than its own mass of the organopolysiloxane, and may contain at least one moiety selected from the group consisting of a polyoxyalkylene moiety, a polyglycerin moiety, an alkyl moiety, an alkenyl moiety, an aryl moiety, and a fluoroalkyl moiety in the molecule. Examples of commercial products thereof include KSG series (available from Shin-Etsu Chemical Co., Ltd.), which are made paste with an oil agent. These crosslinking organopolysiloxanes are not sticky but light feeling and excellent in thickening and stabilizing an oily or W/O cosmetic.

Oily Film-Forming Agents

Examples of the oily film-forming agent include α-olefin/vinyl pyrrolidone copolymers, such as eicosene/vinyl pyrrolidone copolymer; acrylic acid/alkylacrylate copolymer and acryl/silicone graft or block copolymers; and silicone network resins, such as trimethylsiloxy silicate. The silicone network resins to be used may further contain a pyrrolidone moiety, long-chain alkyl moiety, polyoxyalkylene moiety, fluoroalkyl moiety, and anion moiety such as carboxylic acid in the molecule.

Preservatives or Antimicrobials

Examples of the preservative include alkyl para-oxybenzoate, benzoic acid, sodium benzoate, sorbic acid, potassium sorbate, phenoxy ethanol, etc. Examples of the antimicrobial include benzoic acid, salicylic acid, carbolic acid, sorbic acid, alkyl para-oxybenzoate, p-chloro-m-cresol, hexachlorophene, benzalkonium chloride, chlorhexidine chloride, trichlorocarbanilide, photosensitizers, phenoxy ethanol, etc. One or two or more selected from these are used as the preservative or antimicrobial.

Antioxidants etc.

As the antioxidants, one or two or more of antioxidants are selected from tocopherol, butylhydroxyanisol, dibutylhydroxytoluene, phytic acid, etc. Examples of the pH adjusters include lactic acid, citric acid, glycolic acid, succinic acid, tartaric acid, dl-malic acid, potassium carbonate, sodium bicarbonate, ammonium bicarbonate, etc. Examples of the chelating agents include alanine, sodium edetate, sodium polyphosphate, sodium metaphosphate, phosphoric acid, etc. Examples of the cooling agents include L-menthol, camphor, etc. Examples of the anti-inflammatory agent include allantoin, glycyrrhizinic acid and salt thereof, glycyrrhetinic acid and stearyl glycyrrhetinate, tranexamic acid, azulene, etc.

Examples of other agents that can be added as needed include amino acids, such as glycine, serine, arginine, glutamic acid, and derivatives thereof; nicotinic acid and other vitamins; anti-inflammatory agents, such as dipotassium glycyrrhizate; etc. The vitamins include vitamins A, such as vitamin A oil and retinol; vitamins B, such as pyridoxine hydrochloride, panthenol, pantothenyl ethyl ether, nicotinic-acid amide and cyanocobalamins; vitamins C, such as ascorbyl palmitate and ascorbyl glucoside; vitamin E, such as α-tocopherol; and derivatives thereof.

Further, examples of the inventive cosmetic include skin care cosmetics, such as emulsion, cream, cleansing agent, pack, oil liquid, massage material, beauty essence, cleaner, deodorant, hand cream, and lip cream; make-up cosmetics, such as make-up foundation, white powder, liquid foundation, oil foundation, rouge, eye shadow, mascara, eye liner, eyebrow makeup, and lipstick; hair cosmetics, such as shampoo, conditioner, treatment, and setting material; antiperspirant; UV-protective cosmetics, such as sunscreen lotion and sunscreen cream; etc. Moreover, the form of these cosmetics can be selected from various forms, such as liquid, emulsion, cream, solid, paste, gel, powder, pressed, laminated, mousse, spray, and stick forms.

EXAMPLE

Hereinafter, the present invention will be specifically described with reference to Examples and Comparative Examples. However, the present invention is not limited to the following Examples. First of all, high molecular weight polymers (Synthesis Examples 1 to 8) were prepared for use in Examples and Comparative Examples. Note that $M^H$ and D representing siloxane units of organohydrogen polysiloxanes used in the following Synthesis Examples are shown by the following formulae.

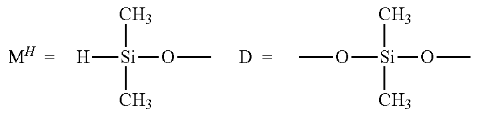

In the formulae, bonding arms bond to other siloxane units.

SYNTHESIS EXAMPLES

First, Synthesis Examples 1 to 8 of high molecular weight polymers will be described.

Production of Compositions

Synthesis Example 1

A three-necked flask was charged with 100 mg of tetrabutylammonium m-chlorobenzoate dried under reduced pressure, and 125 mL of THF was added thereto to dissolve the material. Under nitrogen atmosphere, 2.18 g of dimethylketene methyl trimethylsilyl acetal was added to the mixture, and a monomer mixture (50 g of stearyl methacrylate (SMA), 6.5 g of 2-allyloxyethyl methacrylate, and 50 g of a monomer (a) represented by the following formula) was added dropwise thereto over 30 minutes. After the mixture was further stirred at room temperature for 1 hour, 100 mL of toluene was added and the mixture was washed with water three times. The organic phase was separated and dried over sodium sulfate. After filtration, the solvent was distilled off under reduced pressure at 125° C. for 1 hour to obtain a target polymer crosslinking agent (1). The number-average molecular weight and the polydispersity (Mw/Mn, which is also called molecular weight distribution) (in terms of polystyrene) were measured by GPC. The number-average molecular weight (Mn) was 12,350 (g/mol), and the polydispersity (Mw/Mn) was 1.31.

Next, in a reactor, 3.29 g of organohydrogen polysiloxane represented by an average compositional formula of $M^H_2D_{40}$ (in the general formula (4), two or more $R^8$'s are hydrogen atoms, and the number-average molecular weight was 3,100 (g/mol)), 6.71 g of the polymer crosslinking agent (1) and 23 g of isotridecyl isononanoate were mixed. 10 mg of an ethanol solution containing 3% by mass chloroplatinic acid was added to the mixture. The resulting mixture was stirred at 80° C. for 1 hour to obtain a high molecular weight polymer.

Further, the obtained high molecular weight polymer was kneaded with a three-roll mixer. Then, isotridecyl isononanoate was added thereto for dilution. Thus, a paste-state composition containing 10 mass % of the high molecular weight polymer was obtained.

monomer (a)

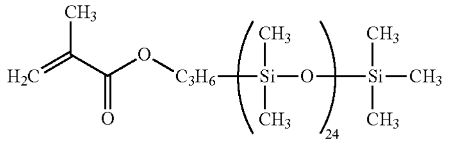

polymer crosslinking agent (1)

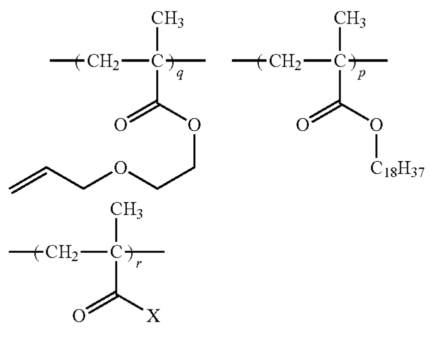

In the formulae, X represents a residue of the monomer (a); "p", "q" and "r" are such numbers that the polymer crosslinking agent has the above-mentioned number-average molecular weight; and each unit shown in parentheses is randomly bonded.

Synthesis Example 2

A three-necked flask was charged with 100 mg of tetrabutylammonium m-chlorobenzoate dried under reduced pressure, and 125 mL of THF was added thereto to dissolve the material. Under nitrogen atmosphere, 2.18 g of dimethylketene methyl trimethylsilyl acetal was added to the mixture, and a monomer mixture (50 g of dodecyl methacrylate (DMA), 6.5 g of 2-allyloxyethyl methacrylate, and 50 g of a monomer (a) represented by the above formula) was added dropwise thereto over 30 minutes. After the mixture was further stirred at room temperature for 1 hour, 100 mL of toluene was added and the mixture was washed with water three times. The organic phase was separated and dried over sodium sulfate. After filtration, the solvent was distilled off under reduced pressure at 125° C. for 1 hour to obtain a polymer crosslinking agent (2). The number-average molecular weight and the polydispersity (Mw/Mn) (in terms of polystyrene) were measured by GPC. The number-average molecular weight (Mn) was 12,030 (g/mol), and the polydispersity (Mw/Mn) was 1.28.

Next, in a reactor, 2.96 g of organohydrogen polysiloxane represented by the average compositional formula of $M^{H}_{2}D_{40}$ (in the general formula (4), two or more $R^8$'s are hydrogen atoms, and the number-average molecular weight was 3,100 (g/mol)), 7.04 g of the polymer crosslinking agent (2), and 23 g of isotridecyl isononanoate were mixed. 10 mg of an ethanol solution containing 3% by mass chloroplatinic acid was added to the mixture. The resulting mixture was stirred at 80° C. for 1 hour to obtain a high molecular weight polymer.

Further, the obtained high molecular weight polymer was kneaded with a three-roll mixer. Then, isotridecyl isononanoate was added thereto for dilution. Thus, a paste-state composition containing 10 mass % of the high molecular weight polymer was obtained.

polymer crosslinking agent (2)

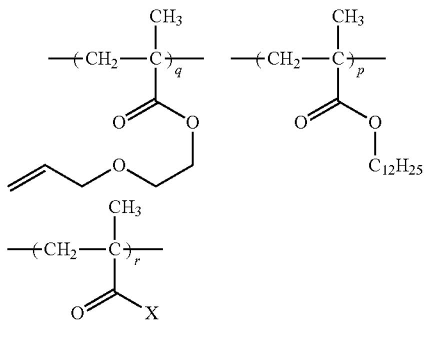

In the formulae, X represents a residue of the monomer (a); "p", "q" and "r" are such numbers that the copolymer has the above-mentioned number-average molecular weight; and each unit shown in parentheses is randomly bonded.

Synthesis Example 3

A three-necked flask was charged with 100 mg of tetrabutylammonium m-chlorobenzoate dried under reduced pressure, and 125 mL of THF was added thereto to dissolve the material. Under nitrogen atmosphere, 2.18 g of dimethylketene methyl trimethylsilyl acetal was added to the mixture, and a monomer mixture (50 g of butyl methacrylate (BMA), 6.5 g of 2-allyloxyethyl methacrylate, and 50 g of a monomer (a) represented by the above formula) was added dropwise thereto over 30 minutes. After the mixture was further stirred at room temperature for 1 hour, 100 mL of toluene was added and the mixture was washed with water three times. The organic phase was separated and dried over sodium sulfate. After filtration, the solvent was distilled off under reduced pressure at 125° C. for 1 hour to obtain a polymer crosslinking agent (3). The number-average molecular weight and the polydispersity (Mw/Mn) (in terms of polystyrene) were measured by GPC. The number-average molecular weight (Mn) was 12,460 (g/mol), and the polydispersity (Mw/Mn) was 1.37.

Next, in a reactor, 3.08 g of organohydrogen polysiloxane represented by the average compositional formula of $M^{H}_{2}D_{40}$ (in the general formula (4), two or more $R^8$'s are hydrogen atoms, and the number-average molecular weight was 3,100 (g/mol)), 6.92 g of the polymer crosslinking agent (3), and 23 g of isotridecyl isononanoate were mixed. 10 mg of an ethanol solution containing 3% by mass chloroplatinic acid was added to the mixture. The resulting mixture was stirred at 80° C. for 1 hour to obtain a high molecular weight polymer.

Further, the obtained high molecular weight polymer was kneaded with a three-roll mixer. Then, isotridecyl isononanoate was added thereto for dilution. Thus, a paste-state composition containing 10 mass % of the high molecular weight polymer was obtained.

polymer crosslinking agent (3)

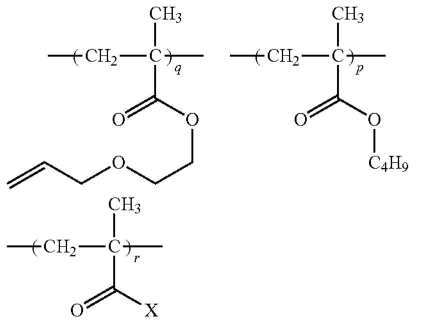

In the formulae, X represents a residue of the monomer (a); "p", "q" and "r" are such numbers that the copolymer has the above-mentioned number-average molecular weight; and each unit shown in parentheses is randomly bonded.

Synthesis Example 4

A paste-state composition containing 20 mass % of the high molecular weight polymer was obtained by the same synthesis method as in Synthesis Example 2, but the solvent of the addition reaction and the dilution solvent after the kneading with a three-roll mixer were changed to triethylhexanoin.

Synthesis Example 5

A paste-state composition containing 20 mass % of the high molecular weight polymer was obtained by the same synthesis method as in Synthesis Example 2, but the solvent of the addition reaction and the dilution solvent after the kneading with a three-roll mixer were changed to cetyl octanoate.

Synthesis Example 6

A paste-state composition containing 20 mass % of the high molecular weight polymer was obtained by the same synthesis method as in Synthesis Example 2, but the solvent of the addition reaction and the dilution solvent after the kneading with a three-roll mixer were changed to glyceryl trioctanoate.

Synthesis Example 7

A paste-state composition containing 20 mass % of the high molecular weight polymer was obtained by the same synthesis method as in Synthesis Example 2, but the solvent of the addition reaction and the dilution solvent after the kneading with a three-roll mixer were changed to cetyl isooctanoate.

Synthesis Example 8

A paste-state composition containing 20 mass % of the high molecular weight polymer was obtained by the same synthesis method as in Synthesis Example 2, but the solvent of the addition reaction and the dilution solvent after the kneading with a three-roll mixer were changed to isopropyl myristate.

Examples 1 to 3, Comparative Examples 1 to 3

<Comparison of Storage Stability>

W/O emulsions were prepared using Synthesis Examples 1 to 3 and, for comparison, (dimethicone/(PEG10/15)) crosspolymer, (PEG-15/lauryl dimethicone) crosspolymer, (PEG-15/lauryl polydimethylsiloxyethyl dimethicone) crosspolymer. The resulting storage stabilities were compared. Note that none of the three crosspolymers used in Comparative Examples contained the repeating units of the formulae (I) to (III). Oil phases were prepared by uniformly mixing 1 to 8 as in Table 1. Then, 9 to 12 were uniformly mixed and dissolved, added to the oil phases, and emulsified by stirring. In this manner, W/O emulsions were prepared.

TABLE 1

| | Example | | | Comparative Example | | |
|---|---|---|---|---|---|---|
| Components | 1 | 2 | 3 | 1 | 2 | 3 |
| 1. high molecular weight polymer composition (Synthesis Example 1) | 10.0 | | | | | |
| 2. high molecular weight polymer canposition (Synthesis Example 2) | | 10.0 | | | | |
| 3. high molecular weight polymer composition (Synthesis Example 3) | | | 10.0 | | | |
| 4. (dimethicone/(PEG-10/15)) crosspolymer (Note 1) | | | | 10.0 | | |
| 5. (PEG-15/lauryl dimethicone) crosspolymer (Note 2) | | | | | 10.0 | |
| 6. (PEG-15/lauryl polydimethy1siloxyethyl dimethicone) crosspolymer (Note 3) | | | | | | 10.0 |

TABLE 1-continued

| | Example | | | Comparative Example | | |
|---|---|---|---|---|---|---|
| Components | 1 | 2 | 3 | 1 | 2 | 3 |
| 7. isotridecyl isononanoate | 13.0 | 13.0 | 13.0 | 13.0 | 13.0 | 13.0 |
| 8. lauryl PEG-9 polydimethylsiloxyethyl dimethicone (Note 4) | 2.0 | 2.0 | 2.0 | 2.0 | 2.0 | 2.0 |
| 9. 1,3-butylene glycol | 10.0 | 10.0 | 10.0 | 10.0 | 10.0 | 10.0 |
| 10. sodium citrate | 0.2 | 0.2 | 0.2 | 0.2 | 0.2 | 0.2 |
| 11. sodium chloride | 0.5 | 0.5 | 0.5 | 0.5 | 0.5 | 0.5 |
| 12. purified water | 64.3 | 64.3 | 64.3 | 64.3 | 64.3 | 64.3 |

(Note 1)
KSG-210 manufactured by Shin-Etsu Chemical Co., Ltd.
(Note 2)
KSG-310 manufactured by Shin-Etsu Chemical Co., Ltd.
(Note 3)
KSG-320Z manufactured by Shin-Etsu Chemical Co., Ltd.
(Note 4)
KF-6038 manufactured by Shin-Etsu Chemical Co., Ltd.

After the emulsions were left standing at 50° C. for 7 days, the appearances were observed to compare the storage stabilities. The results were as shown in Table 2, and the W/O emulsions of the present invention had higher storage stabilities.

TABLE 2

| | Example 1 | Example 2 | Example 3 | Comparative Example 1 | Comparative Example 2 | Comparative Example 3 |
|---|---|---|---|---|---|---|
| Appearance | excellent | excellent | excellent | poor | fair | fair |

excellent: uniform emulsion
fair: the oil phase was slightly separated
poor: the oil phase was separated

Example 4: O/W Type Cream

| | (Components) | mass (%) |
|---|---|---|
| 1. | high molecular weight polymer composition (Synthesis Example 2) | 8.0 |
| 2. | crosslinked methylphenylpolysiloxane (Note 1) | 2.0 |
| 3. | isotridecyl isononanoate | 5.0 |
| 4. | dipropylene glycol | 7.0 |
| 5. | glycerin | 5.0 |
| 6. | methylcellulose (2% aqueous solution) (Note 2) | 7.0 |
| 7. | polyacryl amide-based emulsifier (Note 3) | 2.0 |
| 8. | guanine | 1.0 |
| 9. | preservative | q.s. |
| 10. | fragrance | q.s. |
| 11. | purified water | 63.0 |

(Note 1) manufactured by Shin-Etsu Chemical Co., Ltd.: KSG-18
(Note 2) manufactured by Shin-Etsu Chemical Co., Ltd.: METOLOSE SM-4000
(Note 3) manufactured by SEPPIC S.A.: SEPIGEL 305

(Production Method)

A: Components 4 to 11 were mixed.

B: Components 1 to 3 were mixed, and A was added thereto, stirred, and emulsified.

The cream obtained as described above had tine texture, light spreadability, no stickiness, and no oiliness, but was wet and fresh, and gave refreshing feeling on use. Moreover, it was found that the cosmetic durability was quite well, and the O/W type cream did not change despite temperature change or over time and was excellent in stability.

Example 5: W/O Type Cream

| | (Components) | mass (%) |
|---|---|---|
| 1. | alkyl-crosslinked polyether-modified silicone (Note 1) | 3.0 |
| 2. | high molecular weight polymer composition (Synthesis Example 4) | 4.0 |
| 3. | liquid paraffin | 13.5 |
| 4. | macadamia nut oil | 5.0 |
| 5. | branched silicone co-modified with alkyl and polyether (Note 2) | 0.5 |
| 6. | hybrid silicone composite powder (Note 3) | 3.0 |
| 7. | sodium citrate | 0.2 |
| 8. | propylene glycol | 8.0 |
| 9. | glycerin | 3.0 |
| 10. | preservative | q.s. |
| 11. | fragrance | q.s. |
| 12. | purified water | 59.8 |

(Note 1) manufactured by Shin-Etsu Chemical Co., Ltd.: KSG-310
(Note 2) manufactured by Shin-Etsu Chemical Co., Ltd.: KF-6038
(Note 3) manufactured by Shin-Etsu Chemical Co., Ltd.: KSP-100

(Production Method)

A: Components 1 to 6 were uniformly mixed.

B: Components 7 to 12 were mixed, then added to A, and emulsified.

The cream obtained as described above had no oiliness or stickiness, and spread lightly. Further, the W/O type cream had refreshing feeling and excellent adherence, settled well, and resulted in matte finish.

Example 6: W/O Cream Foundation

| | (Components) | mass (%) |
|---|---|---|
| 1. | high molecular weight polymer composition (Synthesis Example 4) | 4.0 |
| 2. | branched silicone co-modified with polyether and alkyl (Note 1) | 1.0 |
| 3. | triethylhexanoin | 2.0 |
| 4. | cetyl isooctanoate | 5.0 |
| 5. | isotridecyl isononanoate | 9.0 |
| 6. | hybrid silicone composite powder (Note 2) | 3.0 |
| 7. | polyglycerin-co-modified branched silicone (Note 3) | 0.6 |
| 8. | polyglycerin-co-modified branched silicone (Note 4) | 0.3 |
| 9. | alkyl- and silicone-treated pigment (Note 5) | 10.0 |
| 10. | 1.3-butylene glycol | 5.0 |
| 11. | sodium chloride | 0.5 |
| 12. | sodium citrate | 0.2 |
| 13. | preservative | q.s. |
| 14. | fragrance | q.s. |
| 15. | purified water | 59.4 |

(Note 1) manufactured by Shin-Etsu Chemical Co., Ltd.: KF-6038
(Note 2) manufactured by Shin-Etsu Chemical Co., Ltd.: KSP-100
(Note 3) manufactured by Shin-Etsu Chemical Co., Ltd.: KF-6100
(Note 4) manufactured by Shin-Etsu Chemical Co., Ltd.: KF-6105
(Note 5) manufactured by Shin-Etsu Chemical Co., Ltd.: KF-9909

(Production Method)

A: Components 1 to 6 were uniformly mixed.

B: Components 7 to 10 were uniformly mixed.

C: Components 11 to 13 and a portion of Component 15 were mixed and dissolved.

D: B was added to the remainder of Component 15 and homogenized.

E: C was added to A and emulsified.

F: Further, D was added to E emulsified. Finally, Component 14 was added thereto and homogenized.

The cream foundation obtained as described above had no stickiness and spread lightly. Further, the pigment dispersibility was favorable, and the obtained W/O cream foundation had excellent adherence, settled well, and resulted in finish film with quite clean matte appearance.

Example 7: Lipstick

| | (Components) | mass (%) |
|---|---|---|
| 1. | polyethylene wax | 12.0 |
| 2. | microcrystalline wax | 4.0 |
| 3. | polybutene | 5.0 |
| 4. | acrylate/dimethylsilicone copolymer (Note 1) | 12.0 |
| 5. | high molecular weight polymer composition (Synthesis Example 5) | 7.0 |
| 6. | cetyl octanoate | 20.0 |
| 7. | sucrose fatty acid ester | 3.0 |
| 8. | glyceryl triisostearate | 37.0 |
| 9. | pigment | q.s. |
| 10. | preservative | q.s. |
| 11. | fragrance | q.s. |

(Note 1) manufactured by Shin-Etsu Chemical Co., Ltd.: KP-561

(Production Method)

A: Components 5 to 8 were uniformly mixed

B: Components 1 to 4 were dissolved by heating (90° C.), added to A, and homogenized.

C: At 80° C., Components 9 to 11 were added to B and homogenized.

The lipstick obtained as described above had light spreadability, no oiliness, and no powdery texture, and gave refreshing feeling in use. Moreover, the lipstick had favorable water resistance, water repellency, durability, and excellent stability.

Example 8: Eye Shadow

| | (Components) | mass (%) |
|---|---|---|
| 1. | ethylene glycol distearate | 12.0 |
| 2. | high molecular weight polymer composition (Synthesis Example 4) | 5.0 |
| 3. | isotridecyl isononanoate | 35.0 |
| 4. | candelilla wax | 2.0 |
| 5. | Lecithin | 0.2 |
| 6. | hybrid silicone composite powder (Note 1) | 3.0 |
| 7. | alkyl- and silicone-treated pigment (Note 2) | q.s. |
| 8. | mica-treated titanium oxide | balance |

(Note 1) manufactured by Shin-Etsu Chemical Co., Ltd.: KP-6038
(Note 2) manufactured by Shin-Etsu Chemical Co., Ltd.: AES-3083

A: Components 2 to 3 were mixed.

B: Components 6 to 8 were mixed.

C: Components 1, 4 to 5 were mixed, and A was added thereto and heated.

D: C was added to B and poured into a container.

The eye shadow obtained as described above had neither oiliness nor stickiness, spread lightly, and had refreshing usability. Further, the eye shadow had excellent adherence, settled well, and was excellent in make-up durability.

Example 9: Powdery Eyebrow Makeup

| | (Components) | mass (%) |
|---|---|---|
| 1. | Vaseline | 2.5 |
| 2. | dimethylpolysiloxane (6 $mm^2$/sec (25° C.)) | 1.5 |
| 3. | high molecular weight polymer composition (Synthesis Example 6) | 0.5 |
| 4. | glyceryl trioctanoate | 4.0 |
| 5. | silicone-treated mica | 40.0 |
| 6. | silicone-treated talc | balance |
| 7. | silicone-treated titanium oxide | 10.0 |
| 8. | silicone-treated barium sulfate | 15.0 |
| 9. | silicone-treated pigment | q.s. |
| 10. | hybrid silicone composite powder (Note 1) | 1.5 |
| 11. | spherical polymethylsilsesquioxane powder (Note 2) | 2.5 |
| 12. | preservative | q.s. |
| 13. | fragrance | q.s. |

(Note 1) manufactured by Shin-Etsu Chemical Co., Ltd.: KSP-100 (product name)
(Note 2) manufactured by Shin-Etsu Chemical Co., Ltd.: KMP-590 (product name)

(Production Method)

A: Components 5 to 12 were uniformly mixed.

B: Components 1 to 4 were uniformly mixed, added to A, and homogenized.

C: Component 13 was added to B and press-molded with a mold to obtain powdery eyebrow makeup.

The eyebrow makeup obtained as described above had no stickiness, and spread lightly. Moreover, it was found that the powdery eyebrow makeup was excellent in adherence, settled well, and resulted in glossy finish with favorable cosmetic durability.

Example 10: W/O type Antiperspirant

| | (Components) | mass (%) |
|---|---|---|
| 1. | high molecular weight polymer composition (Synthesis Example 6) | 2.0 |
| 2. | crosslinked polyether-modified silicone (Note 1) | 7.0 |
| 3. | decamethylcyclopentasiloxane | 7.0 |
| 4. | glyceryl trioctanoate | 8.0 |
| 5. | 1,3-butylene glycol | 5.0 |
| 6. | sodium citrate | 0.2 |
| 7. | aluminum chlorohydrate | 20.0 |
| 8. | fragrance | q.s. |
| 9. | purified water | 50.8 |

(Note 1) manufactured by Shin-Etsu Chemical Co., Ltd.: KSG-21 (product name)

(Production Method)

A: Components 1 to 4 were mixed.

B: Components 5 to 6 and 9 were mixed, and Components 7 and 8 were added thereto and dissolved.

C: B was added to A, stirred, and emulsified.

The antiperspirant obtained as described above had light spreadability, cool feeling, refreshing feeling, no stickiness, and no greasiness. Moreover, the W/O type antiperspirant did not change due to temperature or over time, and both the usability and stability were quite excellent.

Example 11: O/W type UV Cut Cream

| | (Components) | mass ( %) |
|---|---|---|
| 1. | crosslinked organopolysiloxane (Note 1) | 5.0 |
| 2. | cetyl isooctanoate | 5.0 |
| 3. | high molecular weight polymer composition (Synthesis Example 7) | 1.0 |
| 4. | titanium oxide/decamethylcyclopentasiloxane dispersion (Note 2) | 15.0 |
| 5. | polyether modified silicone (Note 3) | 1.0 |
| 6. | polyether modified silicone (Note 4) | 1.0 |
| 7. | acrylic acid amide-based mixture (Note 5) | 2.0 |
| 8. | propylene glycol | 5.0 |
| 9. | methylcellulose (2% aqueous solution) (Note 6) | 5.0 |
| 10. | preservative | q.s. |
| 11. | fragrance | q.s. |
| 12. | purified water | 60.0 |

(Note 1) manufactured by Shin-Etsu Chemical Co., Ltd.: KSG-18 (product name)
(Note 2) manufactured by Shin-Etsu Chemical Co., Ltd.: SPD-T1S (product name)
(Note 3) manufactured by Shin-Etsu Chemical Co., Ltd.: KF-6027 (product name)
(Note 4) manufactured by Shin-Etsu Chemical Co., Ltd.: KF-6011 (product name)
(Note 5) manufactured by SEPPIC S.A.: SEPIGEL 305 (product name)
(Note 6) manufactured by Shin-Etsu Chemical Co., Ltd.: METOLOSE SM-4000 (product name)

(Production Method)

A: Components 5 to 8, 10, and 12 were mixed.

B: Components 1 to 3 were mixed, added to A, stirred, and emulsified.

C: Components 4 was added to B, and Components 9 and 11 were further added thereto and homogenized.

The UV cut cream obtained as described above had light spreadability, refreshing feeling, transparency, and favorable cosmetic durability, and was neither sticky nor greasy. Moreover, the O/W type UV cut cream did not change due to temperature or over time, and both the usability and stability were quite excellent.

Example 12: W/O type UV Cut Cream

| | (Components) | mass (%) |
|---|---|---|
| 1. | polyether-modified silicone (Note 1) | 1.5 |
| 2. | neopentyl glycol dioctanoate | 2.0 |
| 3. | high molecular weight polymer composition (Synthesis Example 4) | 6.0 |
| 4. | dimethylpolysiloxane (6 $mm^2$/sec (25° C.)) | 2.0 |
| 5. | silica (Note 2) | 0.5 |
| 6. | titanium oxide/decamethylcyclopentasiloxane dispersion (Note 3) | 25.0 |
| 7. | zinc oxide/decamethylcyclopentasiloxane dispersion (Note 4) | 10.0 |
| 8. | dibutylene glycol | 15.0 |
| 9. | sodium citrate | 0.2 |
| 10. | sodium chloride | 0.5 |
| 11. | preservative | q.s. |
| 12. | purified water | 37.3 |

(Note 1) manufactured by Shin-Etsu Chemical Co., Ltd.: KF-6028 (product name)
(Note 2) Godd Ball E-16C
(Note 3) manufactured by Shin-Etsu Chemical Co., Ltd.: SPD-T5 (product name)
(Note 4) manufactured by Shin-Etsu Chemical Co., Ltd.: SPD-Z5 (product name)

(Production Method)

A: Components 1 to 7 were uniformly mixed.

B: Components 8 to 12 were mixed and dissolved.

C: B was added to A and homogenized.

The UV cut cream obtained as described above had light spreadability, refreshing feeling, transparency, and favorable cosmetic durability, and was neither sticky nor greasy. The W/O type UV cut cream did not change due to temperature or over time, and both the usability and stability were quite excellent.

Example 13: W/O/W Type Cream

| | (Components) | mass (%) |
|---|---|---|
| 1. | crosslinked organopolysiloxane (Note 1) | 5.0 |
| 2. | cetyl isooctanoate | 5.0 |
| 3. | high molecular weight polymer composition (Synthesis Example 7) | 1.0 |
| 4. | decamethylcyclopentasiloxane | 5.0 |
| 5. | methyl glucose dioleate | 1.5 |
| 6. | isohexadecane | 3.5 |
| 7. | magnesium sulfate | 0.5 |
| 8. | propylene glycol | 5.0 |
| 9. | purified water | 39.5 |
| 10. | cetyl alcohol | 1.0 |
| 11. | PEG-10 soya sterol | 2.0 |
| 12. | preservative | q.s. |
| 13. | fragrance | q.s. |
| 14. | purified water | 31.0 |

(Note 1) manufactured by Shin-Etsu Chemical Co., Ltd.: KSG-21 (product name)

(Production Method)

A: Components 7 to 9 were mixed.

B: Components 1 to 6 were mixed, added to A, stirred, and emulsified.

C: Components 10 to 12 and 14 were mixed, and B was added thereto under stirring, and emulsified.

D: Component 13 was added to C and homogenized.

The cream obtained as described above had light spreadability, refreshing feeling, transparency, and favorable cosmetic durability, and was neither sticky nor greasy. Moreover, the W/O/W type cream did not change due to temperature or over time, and both the usability and stability were quite excellent.

Example 14: O/W/O type Emulsion

| | (Components) | mass (%) |
|---|---|---|
| 1. | crosslinked organopolysiloxane (Note 1) | 3.0 |
| 2. | glyceryl triisooctanoate | 15.0 |
| 3. | high molecular weight polymer composition (Synthesis Example 6) | 5.0 |
| 4. | sucrose monostearate | 3.0 |
| 5. | glycerin | 5.0 |
| 6. | 1,3-butylene glycol | 5.0 |
| 7. | preservative | q.s. |
| 8. | purified water | 60.0 |
| 9. | macadamia nut oil | 2.0 |
| 10. | cetyl alcohol | 2.0 |
| 11. | fragrance | q.s. |

(Note 1) manufactured by Shin-Etsu Chemical Co., Ltd.: KSG-21 (product name)

(Production Method)

A: Components 1 to 3 were uniformly mixed.

B: Components 4 to 8 were heated and uniformly mixed.

C: Components 9 to 11 were heated and mixed.

D: While B was being stirred, C was added thereto, emulsified, and cooled.

E: While A was being stirred, D was added thereto and emulsified.

The emulsion obtained as described above had light spreadability, refreshing feeling, transparency, and favorable cosmetic durability, and was neither sticky nor greasy. Moreover, the O/W/O type emulsion did not change due to temperature or over time, and both the usability and stability were quite excellent.

Example 15: O/W/O type Liquid Foundation

| | (Components) | mass (%) |
|---|---|---|
| 1. | crosslinked organopolysiloxane (Note 1) | 5.0 |
| 2. | propylene glycol decanoate | 5.0 |
| 3. | isopropyl myristate | 5.0 |
| 4. | pigment | 10.0 |
| 5. | egg yolk-derived hydrogenated phospholipid | 1.0 |
| 6. | glycerin | 2.0 |
| 7. | 1,3-butylene glycol | 10.0 |
| 8. | preservative | q.s. |
| 9. | purified water | 52.0 |
| 10. | squalene | 3.0 |
| 11. | high molecular weight polymer composition (Synthesis Example 8) | 2.0 |
| 12. | cetyl alcohol | 5.0 |
| 13. | fragrance | q.s. |

(Note 1) manufactured by Shin-Etsu Chemical Co., Ltd.: KSG-21 (product name)

(Production Method)

A: Components 1 to 3 were uniformly mixed.

B: Components 4 to 9 were heated and uniformly mixed.

C: Components 10 to 13 were heated and mixed.

D: While B was being stirred, C was added thereto, emulsified, and cooled.

E: While A was being stirred, D was added thereto and emulsified.

The liquid foundation obtained as described above had light spreadability, refreshing feeling, transparency, and favorable cosmetic durability, and was neither sticky nor greasy. Moreover, the O/W/O type liquid foundation did not change due to temperature or over time, and both the usability and stability were quite excellent.

The cosmetics of the present invention each blended with the composition containing the high molecular weight polymer swollen with an ester oil have neither stickiness nor heaviness during the application, are smooth, and spread lightly. After the application, the skin also has light and smooth feelings, for example. The inventive cosmetics have light spreadability and refreshing feeling on use. Accordingly, applying the inventive cosmetics makes it possible to impart flexibility, smoothness, and emollient effect, and give various properties from inherent glossiness to matte appearance, without impairing water evaporation appropriately. With such features, the inventive cosmetics have excellent usability and favorable stability over time.

INDUSTRIAL APPLICABILITY

The inventive cosmetics have light spreadability and refreshing feeling on use. Additionally, the application imparts flexibility, smoothness, and emollient effect. The inventive cosmetics are excellent in a variety of effects ranging from inherent glossiness to matte appearance, have favorable stability over time, and thus are practically quite useful. Moreover, since the inventive compositions are raw-material components of cosmetics actually used, the industrial usefulness is high.

It should be noted that the present invention is not limited to the above-described embodiments. The embodiments are just examples, and any embodiments that substantially have the same feature and demonstrate the same functions and effects as those in the technical concept disclosed in claims of the present invention are included in the technical scope of the present invention.

The invention claimed is:

1. A cosmetic which comprises a composition comprising a high molecular weight polymer swollen with a liquid oil agent, wherein the high molecular weight polymer comprises an addition polymerization product of:

a polymer crosslinking agent comprising a (meth)acrylic-based graft silicone having a main chain with (meth) acrylic-based repeating units represented by the following formulae (I), (II), and (III), and side chains with unsaturated bonds and an organopolysiloxane structure; and an organohydrogen polysiloxane represented by the following general formula (4), (I)

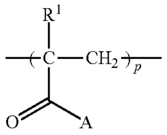

(II)

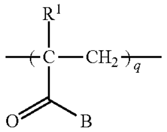

(III)

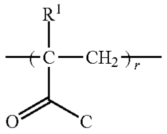

wherein $R^1$'s each independently represent a hydrogen atom or a methyl group;

A represents a group selected from an alkoxy group having 1 to 22 carbon atoms and an aryloxy group having 6 to 20 carbon atoms;

B represents a group having an unsaturated bond represented by the following formula (1), (1)

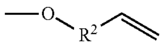

wherein $R^2$ represents a single bond, or a substituted or unsubstituted divalent hydrocarbon group having 1 to 20 carbon atoms and optionally containing an oxygen atom at a position not adjacent to any oxygen in the formula (1);

C represents a group having a linear organopolysiloxane structure represented by the following formula (2), or a group having a dendritic organopolysiloxane structure represented by the following (3-1) or (3-2), (2)

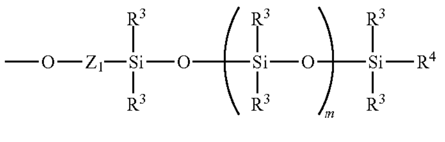

in the formula (2), $Z_1$ represents a divalent organic group, $R^3$'s each independently represent a saturated hydrocarbon group having 1 to 10 carbon atoms or a phenyl group, $R^4$ represents a saturated hydrocarbon group having 1 to 10 carbon atoms, and "m" represents an integer of 0 to 100, (3-1)

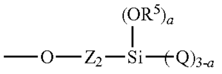

(3-2)

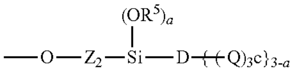

in the formulae (3-1) and (3-2), $Z_2$ represents a divalent organic group, "a" represents a number of 0 to 3, Q represents a group represented by the following formula (3), D represents an organopolysiloxanyl group having a dendritic structure with a hierarchical number of "c" and a valence of $3^c+1$, that is, "3 to the $c^{th}$ power"+1, and "c" represents an integer of 1 to 8, (3)

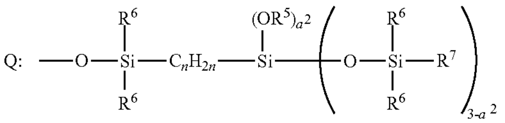

$R^5$ represents a saturated hydrocarbon group having 1 to 10 carbon atoms or a phenyl group, $R^6$ represents a saturated hydrocarbon group having 1 to 8 carbon atoms or a phenyl group, $R^7$ represents a hydrogen atom, a saturated hydrocarbon group having 1 to 10 carbon atoms, or a phenyl group, $a^2$ represents a real number of 0 to 2, and "n" represents an integer of 2 to 12;

an order of bonding of the repeating units represented by the formulae (I), (II), and (III) is not limited;

"q" and "r" are not 0, and "p", "q" and "r" represent integers and are such numbers that the polymer crosslinking agent has a number-average molecular weight of 1,000 to 1,000,000 g/mol;

$$M_xD_yT_zQ_w \quad (4)$$

wherein M represents a siloxane unit of $R^8{}_3SiO_{1/2}$, D represents a siloxane unit of $R^8{}_2SiO_{2/2}$, T represents a siloxane unit of $R^8SiO_{3/2}$, and Q represents a siloxane unit of $SiO_{4/2}$; $R^8$'s each independently represent a hydrogen atom, a substituted or unsubstituted alkyl group having 1 to 10 carbon atoms, or a substituted or unsubstituted aryl group having 6 to 22 carbon atoms; at least two of the siloxane units contain hydrogen atoms; "x", "y", "z", and "w" each represent 0 or a positive number, provided that $y+z+w \geq 1$, and are such numbers that the organohydrogen polysiloxane represented by the general formula (4) has a number-average molecular weight of 500 to 900,000 g/mol; and an order of bonding of the siloxane units represented by M, D, T, and Q is not limited.

2. The cosmetic according to claim 1, wherein C in the repeating unit (III) is a group having a linear organopolysiloxane structure represented by the formula (2).

3. The cosmetic according to claim 1, wherein the liquid oil agent is an ester oil.

4. The cosmetic according to claim 2, wherein the liquid oil agent is an ester oil.

5. The cosmetic according to claim 1, further comprising water, wherein the cosmetic is in a form of emulsion.

6. The cosmetic according to claim 2, further comprising water, wherein the cosmetic is in a form of emulsion.

* * * * *